(12) United States Patent
Hasan et al.

(10) Patent No.: US 8,265,954 B2
(45) Date of Patent: *Sep. 11, 2012

(54) SYSTEM FOR COMMUNICATION OF HEALTH CARE DATA

(75) Inventors: Malik M. Hasan, Las Vegas, NV (US);
J. Dominic Wallen, Tucson, AZ (US);
John C. Peterson, Tucson, AZ (US);
Cindy A. Post, Colton, CA (US); Ralph A. Korpman, San Bernardino, CA (US)

(73) Assignee: HealthTrio LLC, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/161,797

(22) Filed: Jun. 16, 2011

(65) Prior Publication Data
US 2011/0246241 A1    Oct. 6, 2011

Related U.S. Application Data

(63) Continuation of application No. 12/694,041, filed on Jan. 26, 2010, which is a continuation-in-part of application No. 11/925,072, filed on Oct. 26, 2007, (Continued)

(51) Int. Cl.
*G06Q 10/00* (2006.01)

(52) U.S. Cl. ..................... 705/2; 705/3; 705/4

(58) Field of Classification Search ............. 705/2–3
See application file for complete search history.

(56) References Cited

U.S. PATENT DOCUMENTS 4,491,725 A * 1/1985 Pritchard .................. 705/2
(Continued)

FOREIGN PATENT DOCUMENTS
WO    WO 03/036542 A2    5/2003

OTHER PUBLICATIONS

Greg Cooper's e-mail to the Office, dated Apr. 19, 2012.*
(Continued)

*Primary Examiner* — Luke Gilligan
*Assistant Examiner* — Michael Fuelling
(74) *Attorney, Agent, or Firm* — Barnes & Thornburg LLP

(57) ABSTRACT

A computer system that extracts health care data from one or more health care payors to identify meaningful relationships or patterns in treatments to compare the effectiveness of various treatment of specific diseases is provided. This computer system includes a computer and a staging database. The computer is configured to communicate with one or more payor computer systems of a type that includes one or more databases storing records of the health care data from one or more payors over the Internet. The staging database is in communication with the computer and is configured to receive the health care data from each of the payor computer systems. The health care data from each of the payor computer systems is configured to be converted into a normalized format. The normalized data is the made available to determine comparative effectiveness of various treatments of specific diseases.

9 Claims, 14 Drawing Sheets

Related U.S. Application Data now Pat. No. 7,664,660, application No. 13/161,797, which is a continuation-in-part of application No. 11/928,305, filed on Oct. 30, 2007, now Pat. No. 7,707,047, which is a continuation of application No. 11/495,093, filed on Jul. 28, 2006, now Pat. No. 7,440,904, and a continuation-in-part of application No. 10/381,158, filed as application No. PCT/US01/42618 on Oct. 11, 2001, now Pat. No. 7,720,691, said application No. 11/928,305 is a continuation-in-part of application No. 11/495,092, filed on Jul. 28, 2006, now Pat. No. 7,533,030, which is a continuation-in-part of application No. 10/381,158, filed as application No. PCT/US01/42618, said application No. 11/928,305 is a continuation-in-part of application No. 11/495,135, filed on Jul. 28, 2006, now Pat. No. 7,509,264, which is a continuation-in-part of application No. 10/381,158, filed as application No. PCT/US01/42618, said application No. 11/925,305 is a continuation-in-part of application No. 11/494,940, filed on Jul. 28, 2006, now Pat. No. 7,428,494, which is a continuation-in-part of application No. 10/381,158, filed as application No. PCT/US01/42618, said application No. 11/928,305 is a continuation-in-part of application No. 11/494,933, filed on Jul. 28, 2006, now Pat. No. 7,475,020, which is a continuation-in-part of application No. 10/381,158, filed as application No. PCT/US01/42618.

(60) Provisional application No. 60/704,309, filed on Aug. 1, 2005, provisional application No. 60/239,860, filed on Oct. 11, 2000.

(56) References Cited

U.S. PATENT DOCUMENTS

| | | | |
|---|---|---|---|
| 5,359,509 A | | 10/1994 | Little et al. |
| 5,517,405 A | | 5/1996 | McAndrew et al. |
| 5,544,044 A | | 8/1996 | Leatherman |
| 5,557,514 A | | 9/1996 | Seare et al. |
| 5,664,109 A * | | 9/1997 | Johnson et al. ............ 705/2 |
| 5,737,539 A * | | 4/1998 | Edelson et al. ............ 705/3 |
| 5,845,255 A | | 12/1998 | Mayaud |
| 5,924,073 A * | | 7/1999 | Tyuluman et al. ......... 705/2 |
| 6,108,635 A | | 8/2000 | Herren et al. |
| 6,112,183 A | | 8/2000 | Swanson et al. |
| 6,151,581 A | | 11/2000 | Kraftson et al. |
| 6,190,313 B1 * | | 2/2001 | Hinkle ................... 600/300 |
| 6,208,973 B1 * | | 3/2001 | Boyer et al. ............... 705/2 |
| 6,266,675 B1 * | | 7/2001 | Evans et al. ............... 1/1 |
| 6,353,817 B1 | | 3/2002 | Jacobs et al. |
| 6,453,297 B1 | | 9/2002 | Burks et al. |
| 6,475,143 B2 | | 11/2002 | Iliff |
| 6,484,144 B2 | | 11/2002 | Martin et al. |
| 6,802,810 B2 | | 10/2004 | Ciarniello et al. |
| 6,915,254 B1 | | 7/2005 | Heinze |
| 6,988,075 B1 | | 1/2006 | Hacker |
| 7,353,238 B1 * | | 4/2008 | Gliklich ................... 1/1 |
| 7,720,691 B2 * | | 5/2010 | Hasan et al. .............. 705/2 |
| 8,073,710 B2 * | | 12/2011 | Hasan et al. .............. 705/2 |
| 2001/0032099 A1 | | 10/2001 | Joao |
| 2002/0138304 A1 | | 9/2002 | Fontanesi |
| 2003/0212576 A1 | | 11/2003 | Kim |
| 2004/0073460 A1 | | 4/2004 | Erwin |
| 2005/0234740 A1 | | 10/2005 | Krishnan et al. |
| 2005/0288964 A1 | | 12/2005 | Lutzen et al. |
| 2006/0064320 A1 | | 3/2006 | Postrel |
| 2008/0052124 A1 | | 2/2008 | Goodman et al. |
| 2010/0042440 A1 | | 2/2010 | Joao |

OTHER PUBLICATIONS

Attachment to Greg Cooper's e-mail to the Office, dated Apr. 19, 2012.*
International Search Report; Jun. 22, 2011.
Supplementary European Search Report; Application No. EP 06 80 0539;Oct. 13, 2010; (all material itemized in this IDS).
Ledbetter, C.S. et al.: "Toward best practice: leveraging the electronic patient record as a clinical data warehouse." Journal of Healthcare Information Management: JHIM Summer 2001 LNKD-PUBMED: 11452574, vol. 15, No. 2, Jul. 2001.
"HealthTrio integrates SNOMED RT into web-based clinical communication platform" Virtual Medical World; Dec. 5, 2001, pp. 1-2; XP002603557.
Office Action dated Jun. 20, 2007.
Response dated Aug. 10, 2007 to Jun. 20, 2007 Office Action.
Office Action dated Dec. 7, 2007.
Response dated Jun. 6, 2008 to Dec. 7, 2007 Office Action.
Supplemental Amendment dated Aug. 12, 2008.
Office Action dated Feb. 10, 2011.
New Zealand Decision of Assistant of Commissioner of Patents, dated Feb. 9, 2012.
Tom Pullar-Strecker; US attacks computer patents; Fairfax NZ News; Stuff.co.nz; http://www.stuff.co.nz/business/world/6723386/US-attacks-computer-patents, dated Nov. 4, 2012.

* cited by examiner

| # | Organization | Information System | Ann's Information | System Identifier | MPI Identifier |
|---|---|---|---|---|---|
| 1 | Brightbed Hospital | Cerner HIS | Name: Ann Smith DOB: 2/10/1966 | AS12345 | 3243524354235423 |
| 2 | Brightneedle Labs | Misys LIS | Name: Ann Smith DOB: 2/10/1966 | ANNSMI453 | 3243524354235423 |
| 3 | Brightbill Pharmacy | Homegrown IS | Name: Ann Smith DOB: 2/10/1966 | 727-72-2772 | 3243524354235423 |
| 4 | Brightclaim Health Plan | Amisys Claim Processing System | Name: Ann Smith DOB: 2/10/1966 | BC657483301 | 3243524354235423 |
| 5 | Brightgolf Family Care | Millbrook Practice Manager | Name: Ann Smith DOB: 2/10/1966 | AnnSmithe | 3243524354235423 |
| 6 | Bright Stuff Health Network | EPIC Practice Management | Name: Ann Smith DOB: 2/10/1966 | K6465737-01 | 3243524354235423 |

FIG. 7

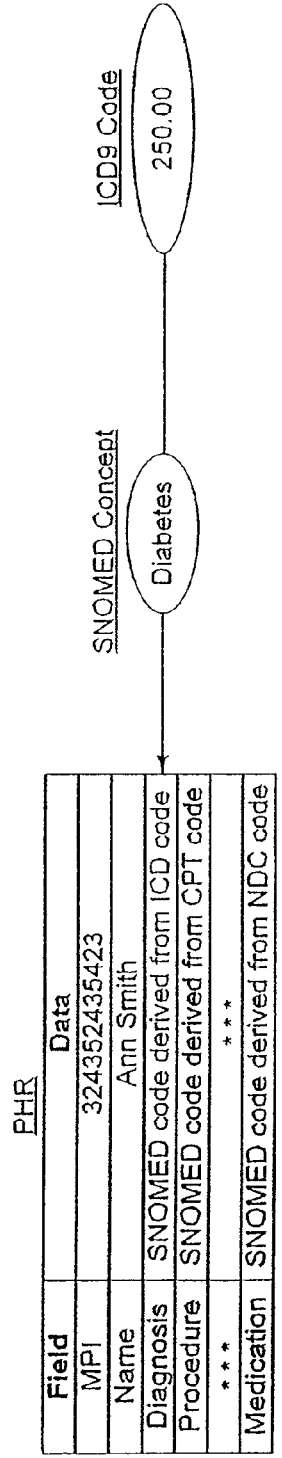

FIG. 9

| C_Medication_Profile | |
|---|---|
| | rowguid |
| FK1,I2,U2 | Profile_Id |
| I3 | Rx_Num_Ext |
| I3 | Pharmacy_Id |
| | Date_Of_Service |
| I3,I1 | Member_Id |
| I1 | Payor_Id |
| | Originator |
| | Type |
| | Status |
| | Start_Date |
| | Last_Filled |
| | End_Date |
| | Refills_Allow |
| | Refills_Remaining |
| | Refill_Number |
| | Label_Name |
| | Brand_Name |
| | Generic_Name |
| | Ndc |
| | Ddid |
| | Dose |
| | Dose_Units |
| | Strength |
| | Strength_Units |
| | Disp_Amt |
| | Disp_Form |
| | Rx_Fill_Amt |
| | Rx_Fill_Form |
| | Rx_Fill_Days |
| | Route_Code |
| | Route_Desc |
| | Sig_Code |
| | Sig_Desc |
| | Reason |
| | Free_Text_Dose |
| | Indication |
| | Changed_Date |
| | Changed_Init |
| | Provider_Id |
| | Provider_Name |
| | Additional_Instructions |
| | Duration_number |
| | Duration_units |
| | Duration_indefinite |
| | Freq_Take_Times |
| | Freq_Take_Every |
| | Freq_Take_Every_Units |
| | Freq_PRN |
| | FDB_dose_form |
| | Dea |
| | SourceSystem |

| C_Allergies | |
|---|---|
| PK | Profile_Id |
| I1 | Member_Id |
| I1 | Payor_Id |
| | Provider_Id |
| | Provider_Name |
| | Originator |
| | Allergy_Code |
| | Allergy_Description |
| | Ndc |
| | Type |
| | Status |
| | Severity_Description |
| | Severity_Code |
| | Allergy_Onset_Description |
| | Allergy_Onset_Code |
| | Reaction_Description |
| | Reaction_Code |
| | Change_Date |
| | Change_Init |
| | entered_date |
| | Reason |
| U1 | rowguid |

| C_Medication_Transaction | |
|---|---|
| PK | ID |
| I1,I2 | HistoryRoot |
| I2 | TDate |
| I1 | AttributeValue |
| | Attribute |
| I1 | profile_type |
| | changeuserid |
| | changememberid |
| | changeproviderid |
| | changeprovidername |
| | payor_id |
| | trans |
| | Originator |
| I2 | GroupCounter |
| | msrepl_tran_version |

| health_entry_source | |
|---|---|
| PK | entity_type_code |
| PK | entity_id |
| PK | claim_xref |
| PK | source_system |
| | payor_id |
| | add_date |
| | SourceCode |
| | SourceCodeType |

FIG. 8E

| Consent | Clinical Permissions | Family Permissions |

Return to Previous Page

Permissions Information

Allbetter, Doctor

Protected Data Classes

These are special categories of data that require patient permissions to access

| Grant | Revoke | Action | Description |
|---|---|---|---|
| ○ | ● | Reproductive Health | On-line access to data related to reproductive health |
| ● | ○ | Mental Health | On-line access to data related to psychological behavior |
| ○ | ● | HIV | On-line access to data related to HIV |
| ○ | ● | Genetic Testing | On-line access to data related to genetic testing |
| ○ | ● | Abortion | On-line access to data related to abortion |
| ○ | ● | Sexually Transmitted Diseases | On-line access to data related to sexually transmitted diseases |

Functional Areas

| Grant | Revoke | Data Group | Description |
|---|---|---|---|
| ○ | ● | Visit Summary | Access your on-line visit summary |
| ○ | ● | My Plan for Health | Access to your on-line my plan for health |
| ○ | ● | Referrals & Authorizations | Access to your referrals and authorizations |
| ○ | ● | Medication Profile | Access your on-line medication profile |
| ○ | ● | Medical History | Access your on-line medical history |

[ Save ]  [ Cancel ]

FIG. 10

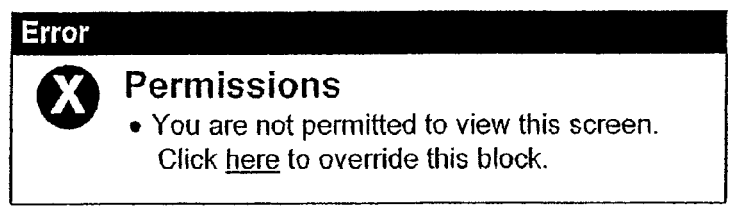

Error

Permissions
- You are not permitted to view this screen.
  Click here to override this block.

FIG. 11

| Override Restrictions | |
|---|---|
| User Information | |
| User ID | 1013 |
| User Name | Doctor Allbetter |
| Transaction Date/Time | 05-Jul-05 |
| • Reason | -Select- ▼ |
| | -or- |
| • Indicates Required Field | Other: |
| Note: | |

Continue   Cancel

FIG. 12

| Audit Permissions Report (reporting period April 20, 2006 – April 22, 2006) | | | | |
|---|---|---|---|---|
| Date/Time | User Name Role Access List | Member Name Member ID | Permission Type | Reason |
| 04-20-06 13:02:00 | Doctor Allbetter Provider Office H Specialist1 | Ann Smith 324352435423 | Consent | To provide routine care and treatment |
| 04-20-06 13:31:05 | Doctor Allbetter Provider Office H Specialist1 | Ann Smith 324352435423 | (FA) My Plan For Health | To provide emergency care |
| 04-20-06 13:52:10 | Doctor Allbetter Provider Office H Specialist1 | Ann Smith 324352435423 | (PDC) HIV | To provide emergency care |
| 04-20-06 14:10:22 | Doctor Allbetter Provider Office H Specialist1 | Ann Smith 324352435423 | (FA) Medication Profile | To provide emergency care |

Print   Close

FIG. 13

SYSTEM FOR COMMUNICATION OF HEALTH CARE DATA

RELATED APPLICATIONS

The present application is a continuation application of, and claims priority to, U.S. patent application Ser. No. 12/694,041, filed on Jan. 26, 2010, entitled "System for Communication of Health Care Data" which is continuation-in-part application of and claims priority to U.S. patent application Ser. No. 11/925,072, filed Oct. 26, 2007, now U.S. Pat. No. 7,664,660 entitled "System for Communication of Health Care Data" which claims priority to U.S. patent application Ser. No. 10/381,158, filed Oct. 6, 2003, entitled "System for Communication of Health Care Data" which is a 371 of PCT/US01/42618, filed Oct. 11, 2001, entitled "System for Communication of Health Care Data" which claims benefit of 60/239,860, filed Oct. 11, 2000, entitled "Apparatus and Method for Establishing Connectivity." This application is also a continuation-in-part application to U.S. patent application Ser. No. 11/928,305, filed Oct. 30, 2007, now U.S. Pat. No. 7,707,047 entitled "Method and System for Generating Personal/Individual Health Records" which claims priority to U.S. Continuation patent application Ser. No. 11/495,093, filed Jul. 28, 2006 (U.S. Pat. No. 7,440,904), entitled "Method and System for Generating Personal/Individual Health Records" which claims benefit of U.S. Provisional Patent Application No. 60/704,309, filed Aug. 1, 2005, entitled "Method and System for Generating Individual Electronic Medical Record" and is a CIP of U.S. patent application Ser. No. 10/381,158, filed Oct. 6, 2003, now U.S. Pat. No. 7,720,691 entitled "System for Communication of Health Care Data" which is a 371 of PCT/US01/42618 filed Oct. 11, 2001, entitled "System for Communication of Health Care Data" which claims benefit of U.S. Provisional Application Ser. No. 60/239,860, filed Oct. 11, 2000, entitled "Apparatus and Method for Establishing Connectivity." application Ser. No. 11/928,305 is a CIP of U.S. patent application Ser. No. 11/495,092, filed Jul. 28, 2006, now U.S. Pat. No. 7,533,030 entitled "Method and System for Generating Personal/Individual Health Records" which claims benefit of U.S. Provisional Application Ser. No. 60/704,309, filed Aug. 1, 2005, entitled "Method and System for Generating Individual Electronic Medical Record" and is a CIP of U.S. patent application Ser. No. 10/381,158, filed Oct. 6, 2003, entitled "System for Communication of Health Care Data" which is a 371 of PCT/US01/42618, filed Oct. 11, 2001, entitled "System for Communication of Health Care Data" which claims benefit of U.S. Provisional Patent Application 60/239,860, filed Oct. 11, 2000, entitled "Apparatus and Method for Establishing Connectivity." application Ser. No. 11/928,305 is also a CIP of U.S. patent application Ser. No. 11/495,135, filed Jul. 28, 2006, now U.S. Pat. No. 7,509,264 entitled "Method and System for Generating Personal/Individual Health Records" which claims benefit of U.S. Provisional Patent Application Ser. No. 60/704,309, filed Aug. 1, 2005, entitled "Method and System for Generating Individual Electronic Medical Record" and is a CIP of U.S. patent application Ser. No. 10/381,158, filed Oct. 6, 2003, entitled "System for Communication of Health Care Data" which is a 371 of PCT/US01/42618, filed Oct. 11, 2001, entitled "System for Communication of Health Care Data" which claims benefit of U.S. Provisional Patent Application Ser. No. 60/239,860, filed Oct. 11, 2000, entitled "Apparatus and Method for Establishing Connectivity." application Ser. No. 11/928,305 is also a CIP of 11/494,940, filed Jul. 28, 2006, (U.S. Pat. No. 7,428,494) entitled "Method and System for Generating Personal/Individual Health Records" which claims benefit of 60/704,309, filed Aug. 1, 2005, entitled "Method and System for Generating Individual Electronic Medical Record" and is a CIP of U.S. patent application Ser. No. 10/381,158, filed Oct. 6, 2003, entitled "System for Communication of Health Care Data" which is a 371 of PCT/US01/42618, filed Oct. 11, 2001, entitled "System for Communication of Health Care Data" which claims benefit of U.S. Provisional Patent Application Ser. No. 60/239,860, filed Oct. 11, 2000, entitled "Apparatus and Method for Establishing Connectivity." application Ser. No. 11/928,305 is also a CIP of 11/494,933, filed Jul. 28, 2006, (U.S. Pat. No. 7,475,020) entitled "Method and System for Generating Personal/Individual Health Records" which claims benefit of U.S. Provisional Patent Application No. 60/704,309, filed Aug. 1, 2005, entitled "Method and System for Generating Individual Electronic Medical Record" and is a CIP of U.S. patent application Ser. No. 10/381,158, filed Oct. 6, 2003, entitled "System for Communication of Health Care Data" which is a 371 of PCT/US01/42618, filed Oct. 11, 2001, entitled "System for Communication of Health Care Data" which claims benefit of U.S. Provisional Patent Application No. 60/239,860, filed Oct. 11, 2000, entitled "Apparatus and Method for Establishing Connectivity." To the extent not included below, the subject matter disclosed in these applications is hereby expressly incorporated into the present application.

FIELD OF THE INVENTION

The present invention relates generally to a computerized system that establishes connectivity between interested parties in the health care industry for the administration of health care services. More particularly, the present invention relates to a system for the normalization of health care data of various formats and exchanging the data in normalized form between insurers and participants, such as providers, patients, and employers.

BACKGROUND AND SUMMARY

Health care can be defined as an information industry; most of the time and money spent in procuring and delivering health care is spent creating, retrieving, or using information. Expenditures on health care information technology support, for example, have increased from about one billion dollars in 1990 to a projected $20 billion in 2000. Yet, even with these investments, it is believed that almost half of all current health care expenditures continue to be for non-patient care activities; a major share of which is for non-automated information support.

Resources having to be directed to non-patient care activities have been endemic in the health care industry since the 1960's. During the 1990's, however, with the demise of Medicare Cost Reimbursement and the rise of managed care, there has been a major shift in attitude and focus among both physicians and patients. New rules now govern the delivery of medical care and the payment for such care. Whether via preferred provider arrangements, capitation arrangements of endless variety, case management, or "best practice" enforcement, determining what care is allowed, what will be paid by whom, and making sure that the appropriate information is submitted to ensure that the process works are now consuming a major share of both time and financial resources of insurers, providers, and patients.

Health care participants, like providers and employers, regularly deal with a number of health care plans from various health insurers. These participants, however, can only obtain information from the insurance companies in limited ways, often making the acquisition of such information quite burdensome. Participants usually only have the telephone, fax, or letter available as a means of communication with the insurers.

Particularly vexing is the timely availability of information from insurers regarding financial transactions, such as eligibility, claims, and benefits, and basic patient-related information, such as medical tests and prescriptions. For example, a provider may seek information from an insurer via a submission form or telephone call to that insurer. In many cases, however, such information is sought or received after the care has been delivered and the patient has left the provider's office. This may result in the delivery of services that are not authorized or covered by the patient's insurer, or may result in other consequences that might impact the type or cost of the services provided.

Another reason for these difficulties is the recent expansion of the "payor" community. At one time, payors consisted of the government (both federal and state) and large insurance companies. Now, a complex array of self-insured plans, IDN's, IPA's, and PPO's, undertaking full or partial capitation, insurance carve-outs, and the like have radically increased the number of users of, and the need for, current information regarding insureds. Most of these entities, both small and large, do spend considerable sums on information systems. Yet, because of the extent of manual processing that exists despite these systems, costs per claim remain substantial.

In addition, payors incur the wrath of their providers and patients by designing complex rules that are difficult or perceived as impossible to administer or follow. Though contrary to this perception, payors do have an interest in providing timely information to providers, patients, employers, and other participants. Still, a significant percentage of a provider's claims are rejected often because they do not comply with all of the rules. These claims require resubmission, telephone calls, and other expensive manual interventions. The dollar costs for this current processing scheme are high. In fact, an entire clearinghouse industry has been developed to provide eligibility (but not benefits) verification services to providers for a fee. Many of the requested verifications, however, cannot be performed at all by such clearinghouses, and those that are performed are often unacceptably cumbersome and, thus, too expensive.

Referral authorizations are often even more complex than claims and such authorization services are generally not available via traditional clearinghouses. Each time a provider writes a prescription, for example, it is written against a formulary specific to that patient's health care plan established by their insurer. Because there are so many formularies, drug prescriptions, too, are often rejected for payment, causing additional work for both the provider and the patient. Similarly, medical tests must be sent to laboratories contracted to support a particular plan, and are reimbursed only when matching complex medical necessity rules.

Many providers do have practice management systems that track encounters and manages billing. None of these systems, however, have the sophistication to accomplish the task of providing all of the information from all the various health insurers in such a cogent form that can be useful to the provider.

Not only providers, but patients, too, spend a majority of their time interacting with the health care system engaged in non-health care activities. This "wasted" time is virtually all related to scheduling appropriate interventions, to waiting for information or services, or to obtaining authorization, reimbursement, or other information for desired or required health care.

The internet has emerged as a major source of health care information for the public. A substantial portion of internet users use it for health care information or management. Specifically, patients search the internet for medical information and answers related to their area of concern. In fact, it is becoming common for a patient to enter a physician's office armed with printouts and long lists of questions and recommendations from web pages on the internet.

Unfortunately, even with the connectivity the internet provides, information exchange between insurers and patients is lacking. Most of the information available to patients from their insurer is on an automated basis from databases related to either general health care literature or to specific normality support groups. A critical aspect of the patient's health care program, however, is not only knowledge of the normality or support groups, but also what their insurer's health care plan provides as treatment options for that normality, eligibility information, referral authorization, claim submission and payment, testing, and medications. As discussed, these functionalities are too complicated for the current system to handle in an automated environment. Personally-referenced information linked to an individual patient's provider and health care plan is generally unavailable, because that data exists in several databases often each in a different, incompatible format, requiring human intervention to extract and process the data. The patient's current solution is, thus, an endless number of telephone calls at a high cost in dollars, time, and frustration.

A reason for such incompatibility is that each database served the individual needs of those using the data before such a time when connectivity between databases was a consideration. The consequence of having different databases of different formats is that it is not possible to provide a central repository of homogenized data readable by any variety of computers. It is this incompatibility that prevents wide spread connectivity between insurers and participants.

Transliterating and interfacing programs are known in the art. Programs that take data in one format can be translated and read by a computer of a different format. Such transliterating, however, only shifts data from a field of an incompatible format to a target field of a new format. It cannot determine whether the data of the incompatible format is being transferred to the correct target field. Normalization or remodeling of the data not only transfers the data, but also determines the meaning of the data and puts that data in the correct field.

It would, therefore, be beneficial to provide a system with which insurers may communicate with providers, patients, etc., to provide information about a particular health care plan either before, or contemporaneously with, the patient's visit to the provider, regardless the lack of compatibility of the databases. It would be further beneficial if this system of communication spanned a variety of insurers so the provider, for example, may communicate with any plan in which the patient participates. It would also be beneficial for providers to have an automated system of determining eligibility and benefits, receiving authorizations and pre-certifications, submitting claims, obtaining reimbursements, and adjudicating claim problems through the normalization of data of the incompatible databases.

In addition, there is a substantial distinction between an electronic medical record ("EMR") and a personal health record ("PHR"), which is also commonly called an individual health record ("IHR"). The terms "PHR" and "IHR" are interchangeably used herein.

An EMR is provider-centric while a PHR is patient-centric. An EMR is not a complete health record of a patient, but is limited in scope to a specific health care provider. Notably, the electronic medical record does not contain any information from any other health care provider who does not have access or share the same specific EMR.

Electronic medical records are known. Typically, the EMR is established by hospitals or a group of physicians or less commonly by a physician. The EMR details each encounter between the patient and the provider for each episode of illness treated by the specific provider (hospital, physicians, or other care givers). Although the EMR is the commonly looked to as the medico legal record of that particular episode of illness and its management, it does not contain any information from any other provider who does not have access or share the same specific EMR.

A patient has no control over his/her EMR. For example, patients have no direct online access to their EMR and cannot make any entries in the record. Patients have no control over the access to their EMR and anyone who has access to the EMR of the specific hospital or physician group could access their health records. There is no complete global unified record of a patient in an EMR unless and until the entire healthcare is being delivered by the one provider group who is using the specific EMR for all patient encounters. The EMR system usually is used by a limited number of users (providers).

Accordingly, an illustrative embodiment of the present disclosure provides an apparatus for communicating health care data from a sender to a receiver. The apparatus comprises a first computer system, a second computer system, and a rules engine. The first computer system having health care data stored therein. The second computer system is in operable communication with, and is configured to extract the health care data from the first computer system. The rules engine normalizes the extracted health care data to a predefined format. The rules engine defines a plurality of health care data fields in the predefined format, as well as a plurality of relationships between fields of normalized data.

Further embodiments may include the first computer being a plurality of computers each having portions of the health care data stored thereon. The apparatus may also comprise a third computer system, in operable communication with, and configured to receive the normalized data from, the second computer system. The rules engine may determine whether the third computer is authorized to receive the health care data.

Another illustrative embodiment provides a method for communicating health care data from one computer system to another. The method comprises the steps of storing health care data in a first computer system; extracting health care data from the first computer system and communicating the extracted data to a second computer system; normalizing the extracted data to a predefined format in accordance with a rules engine that defines a plurality of health care data fields in the predefined format and a plurality of relationships between fields of normalized data; and communicating the normalized data to a third computer system.

Further embodiments of the illustrative method may include the first computer system comprising a plurality of computers, wherein the storing step includes storing health care data in more than one of said computers. Also, the third computer system comprises a plurality of computers. The health care data exists across a plurality of databases such that each of the plurality of databases are in operable communication with the second computer system.

Another illustrative embodiment provides a system of exchanging health care data between a sender and a receiver. The system comprises a sender computer, an intermediary computer, a rules engine and a receiver computer. The sender computer stores the health care data. The intermediary computer is in operable communication with the sender computer and is configured to extract the health care data. The extracted data is normalized to a predefined format, creating normalized data pursuant to a rules engine. The rules engine defines each field of the health care data and converts each field to a corresponding field in the predefined format. The rules engine also defines how the normalized data should relate to each other pursuant to predetermined instructions. The receiver computer is in operable communication with the intermediary computer. The receiver computer receives the normalized data subjected to the second rules engine.

Further embodiments may include the sender computer being a plurality of computers each having portions of the health care data stored thereon. The rules engine may determine whether the receiver computer is authorized to receive the health care data. When the receiver is a health care provider, the normalized data exchanged between the sender and receiver may be chosen from a group comprising eligibility/benefit display, member roster, claim submission, provider lookup, formulary lookup, diagnosis code lookup, procedure code lookup, access health plan information online, communicate with a health plan on-line, communicate with patients on-line, patient-centric view of data across several health plans, order generation and tracking, results review and release, result printing, prescription writing, medication profile for each patient, access to patient's personal health record based on patient approval, personalized medical and health care content integration, both context-specific and on demand, e-commerce integration: office, medical and health-related product awareness and buying capabilities, email, practice management system subscription, support disease management, and physician credentialing subscription. When the receiver is an employer, the normalized data exchanged between the sender and receiver is chosen from a group comprising group eligibility, group enrollment, enrollment changes, formulary lookup, e-commerce integration, access from health plan web site or direct access via URL, personalized content integration, both context-specific and on demand, e-commerce integration and health care-related product awareness and buying capabilities.

When the receiver is a patient, the normalized data exchanged between the sender and receiver is chosen from a group comprising identification card requests, address changes, provider directory inquiries, personalized health information based on an interest profile, diagnosis information, relevant articles and patient education materials, communications from health care providers and health care plans, lab and radiology results, scheduled appointments with a health care provider, prescription refills, personal health records, eligibility/benefit information, claim information, referral and authorization information and status, provider lookup, family history, medication profile and formulary lookup.

Another illustrative embodiment of the present invention provides a system of normalizing health care data for transfer between an insurer and a participant. The system comprises an insurer system, an intermediary system, and a participant system. The insurer system is configured to maintain at least one database comprising the health care data. The intermediary system is operatively connected to the insurer system and to the database, configured to extract the health care data from the database of the insurer system, and store the health care data in a staging database as extracted data. The extracted data is normalized to a predefined format, creating normalized data pursuant to a rules engine that defines each field of the extracted data in the predefined format. The rules engine also defines how the normalized data relates to each other pursuant to predetermined instructions. The participant system is in operable communication with the intermediary system, and is configured to receive the normalized data subject to the rules engine.

Further embodiments of the illustrative system may include the at least one database being a plurality of databases, such that the intermediary system is operatively connected to the plurality of databases. In addition, the participant system may transmit a request that is sent to the intermediary system that determines which health care data is to be extracted and normalized in order to respond to the request. The participant system may also transmit the request, and the intermediary system may transmit the normalized data over the interne. The rules engine may define the relationships among the normalized data pursuant to predetermined instructions to determine a response to the request. The intermediary system may also comprise an error data system that removes extracted data identified as invalid when the extracted data is normalized. The extracted data identified as invalid is then corrected, reintroduced, and is normalized. The intermediary system may further comprise an audit database to track the activity of the intermediary system.

Another illustrative embodiment of the present invention provides a system of health care management of medical testing administration between an insurer, a medical laboratory, and at least one health care participant. The system comprises a participant computer, an insurer processing system, a rules database, and a laboratory computer. A medical test request is made at the participant computer pursuant to a first predetermined format. The insurer processing system is operatively coupled to the participant's computer, and is through which the medical request is transferred. The processing system is operatively coupled to the rules database to approve the medical test request pursuant to predetermined criteria. The laboratory computer is operatively coupled to the processing system and receives the medical test request if approved by the rules engine. Results of the medical test are transmitted from the laboratory computer to the processing system. The results are further transmitted to an insurer computer that is operatively coupled to the laboratory computer and to participant's computer.

Further embodiments of the illustrative system may include the processing system converting the results of the medical test to a second predetermined format readable by a database stored on the insurer computer. In addition, at least one health care participant may be chosen from a group comprising from a health care provider, an employer, and a patient. Furthermore, the medical test request and the results of the medical test may be transmitted through the internet.

The present invention is not merely a system for electronically storing and accessing medical records, but relates to computerized systems and methods, including software attendant thereto, for generating a personal health record ("PHR"), also described as an Individual Health Record or Electronic Health Record (hereafter "IHR" or "EHR"). In contrast to an EMR, the PHR contemplated herein is intended to include all relevant health-related information for a patient, regardless of the specific health care provider. The clinical information regarding the individual patient may be collected from diverse sources including, but not limited to information from claims through the health plans, multiple EMR's being used from different providers providing care to that patient, medication records from the pharmacy benefit managers ("PBMs"), information from labs and imaging centers, and direct input by the patient to provide a unified personal/individual health record. The PHR may contain health records of millions of patients with online access to those millions of patients.

In one embodiment, the invention provides a system and method for generating a personal/individual health record that is compiled from diverse sources, such as patient questionnaires or direct input, health plans, pharmacy benefits managers ("PBMs"), labs, imaging centers, freestanding outpatient facilities, hospitals and physicians. The data collected from the diverse sources is organized into an individual health record for a patient. The individual health record may be integrated with SNOMED codes to allow that data to be encoded under specific medical diagnostic concepts. SNOMED is a division of the College of American Pathologists ("CAP"). SNOMED Clinical Terms ("SNOMED CT") is a scientifically-validated, clinical health care terminology and infrastructure. Health data can be captured, shared and aggregated in a consistent manner by the SNOMED CT terminology. The terminology currently contains over 350,000 hierarchically specified health care concepts, each with unique meanings and logic-based definitions. Additionally, these health care concepts have distinct relationships that support reliability and consistency for data retrieval. As used herein, the term "universal health care concept codes" means a common language that enables a consistent way of indexing, storing, retrieving, and aggregating clinical data across specialties and sites of medical care. Each "universal health care concept code" is a unique identifier indicative of a node in a hierarchy of health care concepts to which other types of medical data can be mapped. The term "universal health care concept code" is intended to be synonymous with the term "SNOMED code."

In some embodiments, security and medical privacy could be provided such that a patient could have the ability to permit the entire individual health record to be viewed by designated persons or only permit selected parts of the record to be viewed by the authorized persons. This authorization is based on the ability of a patient to block any information relating to a protected class (e.g., mental health, reproductive system conditions in a female or STD, etc.) and/or functional area (e.g., illness/condition list, procedure list, medication profile, etc.). Any part of the record relating to that protected class and/or functional-area could be blocked and continued to be automatically blocked until a change is made by the patient.

According to another aspect, the invention provides a method for generating a personal/individual health record. The method may include the act of receiving a data element indicative of a health related parameter for a patient. The act of determining a SNOMED code corresponding to the data element may be included in the method. An entry may be inserted into a personal/individual health record associated with the patient based on the determined SNOMED code.

In some illustrative embodiments, the data element may include payor claims data. For example, the data element may be a health insurance claim code. Depending on the exigencies of a particular application, the data element may include patient questionnaires or direct input, health plans, pharmacy benefits managers ("PBMs"), labs, imaging centers, freestanding outpatient facilities, hospitals and physicians. Embodiments are also contemplated in which the data element may include an ICD code, a CPT code, a NDC code, LOINC code, or a code from a proprietary coding system, such as Lapcorps' lab and order codes.

The method may include the act of transmitting a description of the entry to a client system in some embodiments. In some cases, a first description and a second description may be associated with the entry. In such embodiments, the first description could be synonymous with the second description. For example, the first description may use medical terminology whereas the second description could use layman's terms. Preferably, the first description is transmitted if the client system is associated with a healthcare provider whereas the second description is transmitted if the client system is not associated with a health care provider.

In some illustrative embodiments, the method may include the act of determining whether the individual health record includes any entries related to the new entry. Preferably, any entries in the individual health record that are related to the entry are associated based on the determined SNOMED code.

According to another aspect, the invention provides a data processing system with a messaging facility configured to receive a data element indicative of a health related parameter for a patient. The system may include a correlation module configured to determine a SNOMED code corresponding to the data element. A PHR population engine may be operably associated with the correlation module, such that the PHR population engine is configured to insert health related data associated with the SNOMED code into a personal/individual health record associated with the patient.

In some embodiments, the system may include an access management module configured to communicate with a client system. In some cases, the access management module could be configured to transmit a description of the health related data to the client system. For example, the PHR population engine may associate more than one synonymous description with the health related data. Embodiments are contemplated in which some of the descriptions use medical terminology and others use layman's terms.

The system may include a filtering module in some embodiments. Typically, the filtering module may be configured to determine whether the client system is associated with a healthcare provider. The description transmitted to the client system may differ depending on whether the client system is associated with a healthcare provider. In some embodiments, the filtering module may be configured to change the description of the health related data based on a description of a SNOMED code up a SNOMED hierarchy to adjust the resolution of data.

In some embodiments, the system may include a PHR database configured to store a plurality of individual health records. The system may also include a data analysis module configured to identify patterns or relationships among the plurality of individual health records in the PHR database based on related SNOMED codes. For example, the data analysis module may be configured to measure effectiveness of healthcare treatment based on outcomes associated with the plurality of individual health records having related SNOMED codes. In some cases, the data analysis module may be configured to perform population studies based on SNOMED codes in the plurality of individual health records.

Embodiments are also contemplated in which the data analysis module may be configured to analyze a health care provider's quality of care and cost. For example, the data analysis module may profile health care providers based on patient outcomes associated with the health care providers. Likewise, the health care providers could be profiled in terms of costs, such as the cost charged by health care providers for various procedures. Health care providers could thus be ranked based on quality of care and cost. This information could allow various payors, such as insurance companies or governmental entities, to establish a list of preferred health care providers based on a formula that includes objective measures for quality of care and cost, as well as possibly other factors.

According to a further aspect, the invention provides a method of generating a personal/individual health record. The method may include the act of receiving a claims data element indicative of a health insurance claim associated with a patient. The SNOMED code corresponding to the claims data element may be determined. The method may also include inserting the SNOMED code into a personal/individual health record associated with the patient.

In some embodiments, the method may include the act of receiving a questionnaire data element indicative of an answer to a questionnaire by the patient. A SNOMED code corresponding to the questionnaire data element may be determined and inserted into the individual health record associated with the patient. Embodiments are also contemplated in which the method includes the act of receiving a clinical data element indicative of clinical data associated with the patient. In such embodiments, a SNOMED code corresponding to the clinical data element may be determined and inserted into the individual health record associated with the patient.

According to another aspect, the invention provides a method for generating a personal/individual health record. The method may include the act of receiving a data element indicative of a health related parameter for a patient. A health related concept that corresponds to the data element may be identified, such that the health related concept is selected from a hierarchical arrangement of health related concepts. A new entry may be inserting into the individual health care record that is representative of the identified health related concept. Also, the new entry may be associated with entries in the individual health record that have a hierarchical relationship to the new entry.

In some embodiments, the hierarchical arrangement includes nodes representative of medical diagnoses or medical procedures. For example, the hierarchical arrangement may include at least 300,000 nodes, such as a plurality of SNOMED Clinical Terms.

According to a further aspect, the invention provides a computer-readable medium having a data structure stored thereon. The data structure may include a diagnosis data field for storing a plurality of diagnosis data elements representative of medical diagnoses associated with a patient. For example, at least one diagnosis data element may be derived from a payor diagnosis code based on a SNOMED code. A procedure data field for storing a plurality of procedure data elements representative of medical procedures associated with the patient may also be included in the data structure. Preferably, at least one procedure data element is derived from a payor procedure code based on a SNOMED code. In some cases, the data element may be manually entered.

In some embodiments, a diagnosis data element may be derived from an ICD code. Embodiments are also contemplated in which a procedure data element may be derived from a CPT code. Other embodiments are contemplated in which other health-related information could be derived from other types of codes, such as LOINC codes or proprietary codes, such as Lapcorbs' lab and order codes.

Depending on the particular application, the data structure may include a medication data field for storing a plurality of medication data elements representative of medications associated with the patient. For example, a medication data element may be derived from a health insurance medication code based on a SNOMED code. In some cases, a medication data element may be derived from a NDC code. In some embodiments, the procedure data element may be derived from a questionnaire answered by the patient based on a SNOMED code associated with an answer to the questionnaire.

A still further aspect of the invention is achieved by a computer-usable medium having computer readable instructions stored thereon for execution by a processor to perform a method. In some cases, the method includes the act of receiving a claims data element indicative of a health insurance claim associated with a patient. A SNOMED code corresponding to the claims data element may be determined and inserted into a personal/individual health record associated with the patient. The method may include the act of receiving a questionnaire data element indicative of an answer to a questionnaire by the patient. The SNOMED code corresponding to the questionnaire data element may be determined and inserted into the individual health record associated with the patient. The method may include the act of receiving a clinical data element indicative of clinical data associated with the patient. The SNOMED code corresponding to the clinical data element may be determined and inserted into the individual health record associated with the patient.

According to another aspect, the invention provides a method for selectively restricting access to a personal/individual health record. The method may include associating an access list for each user capable of accessing a personal/individual health record associated with a patient, such that the access list categorizes the individual health record into a restricted set of data elements and an accessible set of data elements. A request may be received from a user for a data element in the individual health record. The method may include the act of determining whether the data element is in the restricted set of data elements by reviewing an access list associated with the user. If the data element is in the restricted set of data elements, access to the data element will be denied. However, if the data element is in the accessible set of data elements, the user will be allowed to access to the data element. In some embodiments, a predetermined list of possible restricted areas may be presented to a patient. The access list may be created responsive to selections by the patient.

According to a further aspect, the invention provides a method for generating a individual health record, in which the desired information from each source is pre-selected so as to collect information which is important and necessary for the continuing care of a patient and thus avoid massive accumulation of data in the patient's individual health record, which has none or little relevance to continuing care. This allows the user not to spend excessive amounts of time scrolling through lots of data to find actionable information. For example, a massive amount of information is typically collected in an EMR following an inpatient admission, such as extensive nursing reports, voluminous lab results, information regarding the scheduling of tests and procedures during the hospitalization. In some cases, the information which is imported in the PHR may be less than ten percent of the EMR and include only pre-selected types of data, such as the admission history and physical exam, discharge summary and discharge plans, and surgical report and pre-selected test results such as MRI, CT-Scans, and angiography results.

A further aspect of the invention is achieved by a method for generating a personal/individual health record. The method may include the act of receiving payor claims data associated with a patient. Encounter data indicative of an encounter between the patient and a health care provider may be derived from the payor claims data. A new entry may be inserted into a personal/individual health record associated with the patient based on the encounter data. In some embodiments, the deriving step may include deriving a primary care physician encounter history, an outpatient encounter history and a hospital admissions history from the payor claims data.

According to another aspect, the invention provides a method of filtering data in a personal/individual health record. The method may include receiving a request from a health care provider for a personal/individual health record associated with a patient. A specialty associated with the health care provider may be identified. The data elements in the individual health record that relate to the specialty of the health care provider may be determined. In response to the request, the health care provider may be presented with any data elements in the individual health record that were determined to relate to the specialty.

Another illustrative aspect includes computer system that extracts health care data from one or more health care payors to identify meaningful relationships or patterns in treatments to compare the effectiveness of various treatment of specific diseases. This computer system comprises a computer and a staging database. The computer is configured to communicate with one or more payor computer systems from one or more payors over the Internet. The payor computer systems are of a type that includes one or more databases storing records of the health care data. A normalized format is of a type that displays health care data from one or more sources such that any health care data having the same meaning will be expressed in the same format despite any prior formatting. The staging database is in communication with the computer and is configured to receive the health care data from each of the payor computer systems. The health care data from each of the payor computer systems is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format. Lastly, the normalized data is made available to determine comparative effectiveness of various treatments of specific diseases.

Another aspect includes a computer system that extracts health care data from one or more health care payors to identify meaningful relationships or patterns in treatments across multiple payors to compare the effectiveness of various treatments of specific diseases. This computer system comprises a computer and a staging database. The computer is configured to communicate with one or more payor computer systems from one or more payors over the Internet. The payor computer systems are of a type that includes one or more databases storing records of the health care data. A normalized format is of a type that displays health care data from one or more sources such that any health care data having the same meaning will be expressed in the same format despite any prior formatting. The staging database in communication with the computer and is configured to receive the health care data from each of the payor computer systems. The health care data from each of the payor computer systems is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format. Lastly, the normalized data is made available to determine comparative effectiveness of various treatments of specific diseases and to allow to set up or modify clinical protocols for optimal care.

Another aspect includes a computer system that extracts health care data from a health care payor to identify meaningful relationships or patterns in treatments which are not optimal for quality care. This computer system comprises: a staging database in communication with the computer configured to receive health care data from a payor legacy computer system; wherein the payor legacy computer system is of a type that includes one or more databases storing records of the health care data; wherein a normalized format is of a type that displays health care data from one or more sources such that any health care data having the same meaning will be expressed in the same format despite any prior formatting; wherein the health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format; and wherein the normalized data is made available to set up or modify clinical care management protocols to deliver optimal care.

Another aspect includes a computer system that extracts health care data from a health care payor to identify meaningful relationships or patterns in treatments across multiple providers for improving quality of care. This computer system comprises a staging database configured to receive health care data from a payor legacy computer system. The payor legacy computer system is of a type that includes one or more databases storing records of the health care data. A normalized format is of a type that displays health care data from one or more sources such that any health care data having the same meaning will be expressed in the same format despite any prior formatting. The health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format. Lastly, the normalized data is made available to allow to set up or modify a case management based on clinical protocols to provide optimal care.

Another aspect includes a computer system that extracts health care data from a health care payor to identify meaningful relationships or patterns in treatments of chronic diseases which may be suboptimal. This computer system comprises a staging database configured to receive health care data from a payor legacy computer system. The payor legacy computer system is of a type that includes one or more databases storing records of the health care data. A normalized format is of a type that displays health care data from one or more sources such that any health care data having the same meaning will be expressed in the same format despite any prior formatting. The health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format. Lastly, the normalized data is made available to improve disease management of chronic diseases.

Another aspect includes a computer system that identifies meaningful relationships or patterns in treatments to identify effectiveness of specific treatments of diseases for improving quality of care. The computer system comprises a computer that includes one or more records of health care data and configured to convert the health care data into a normalized format. The normalized format is of a type that displays health care data from one or more sources such that any health care data having the same meaning will be expressed in the same format despite any prior formatting. Converting the health care data into the normalized format is done so by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format. Lastly, the normalized data is made available to determine effectiveness of various specific disease treatments to identify effective disease treatments for cost and quality of care.

Another aspect includes a computer system that identifies meaningful relationships or patterns in treatments to identify effectiveness of specific treatments of diseases for improving quality of care. The computer system comprises a computer configured to communicate with a payor computer system over the Internet. The payor computer system is of a type that includes one or more databases storing records of the health care data. A normalized format is of a type that displays health care data from one or more sources such that any health care data having the same meaning will be expressed in the same format despite any prior formatting. A staging database communicates with the computer and configured to receive the health care data from the payor computer system. The health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format. The normalized data includes health care payor data and is made available to determine effectiveness of various specific disease treatments to identify effective disease treatments for cost and quality of care to allow clinical protocols to be set up to optimize care.

Another aspect includes a computer system that identifies meaningful relationships or patterns in treatments to identify effectiveness of specific treatments of diseases for improving quality of care. The computer system comprises a computer configured to communicate with payor computer system over the Internet. The payor computer system is of a type that includes one or more databases storing records of the health care data. A normalized format is of a type that displays health care data from one or more sources such that any health care data having the same meaning will be expressed in the same format despite any prior formatting. A staging database communicates with the computer. The staging database is configured to receive the health care data from the payor computer system. The health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format. The normalized data includes health care provider data and is made available to determine effectiveness of various specific disease treatments to identify effective disease treatments for cost and quality of care to allow clinical protocols to be set up to optimize care.

Another aspect includes a computer system that identifies meaningful relationships or patterns in treatments to identify effectiveness of specific treatments of diseases for improving quality of care. The computer system comprises a computer configured to communicate with a payor computer system over the Internet. The payor computer system is of a type that includes one or more databases storing records of the health care data. A normalized format is of a type that displays health care data from one or more sources such that any health care data having the same meaning will be expressed in the same format despite any prior formatting. A staging database communicates with the computer and is configured to receive the health care data of the payor computer system. The health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format. The normalized data includes health care claims data and is made available to determine effectiveness of various specific disease treatments to identify effective disease treatments for cost and quality of care to allow clinical protocols to be set up to optimize care.

Additional features and advantages of the system will become apparent to those skilled in the art upon consideration of the following detailed descriptions exemplifying the best mode of carrying out the system as presently perceived.

BRIEF DESCRIPTION OF THE DRAWINGS

The illustrative system will be described hereinafter with reference to the attached drawings which are given as non-limiting examples only, in which:

FIG. 7 shows an example table using a MPI identifier according to an embodiment of the present invention;

FIGS. 8A-8E show a database diagram illustrative of a portion of one embodiment of a system and method according to the present invention;

FIG. 9 shows a block diagram of a portion of an embodiment of the present invention;

FIG. 10 shows an example window in which access control for the individual health record may be established;

FIG. 11 shows an example window denying permission to access a portion of the individual health record;

FIG. 12 shows an example window in which a user may override a restriction to a personal/individual health record;

FIG. 13 shows an example audit report that may be generated by the system according to an embodiment of the present invention.

Corresponding reference characters indicate corresponding parts throughout the several views. The exemplification set out herein illustrates an embodiment of the invention, and such exemplification is not to be construed as limiting the scope of the invention in any manner.

DETAILED DESCRIPTION OF THE DRAWINGS

Figure 1:
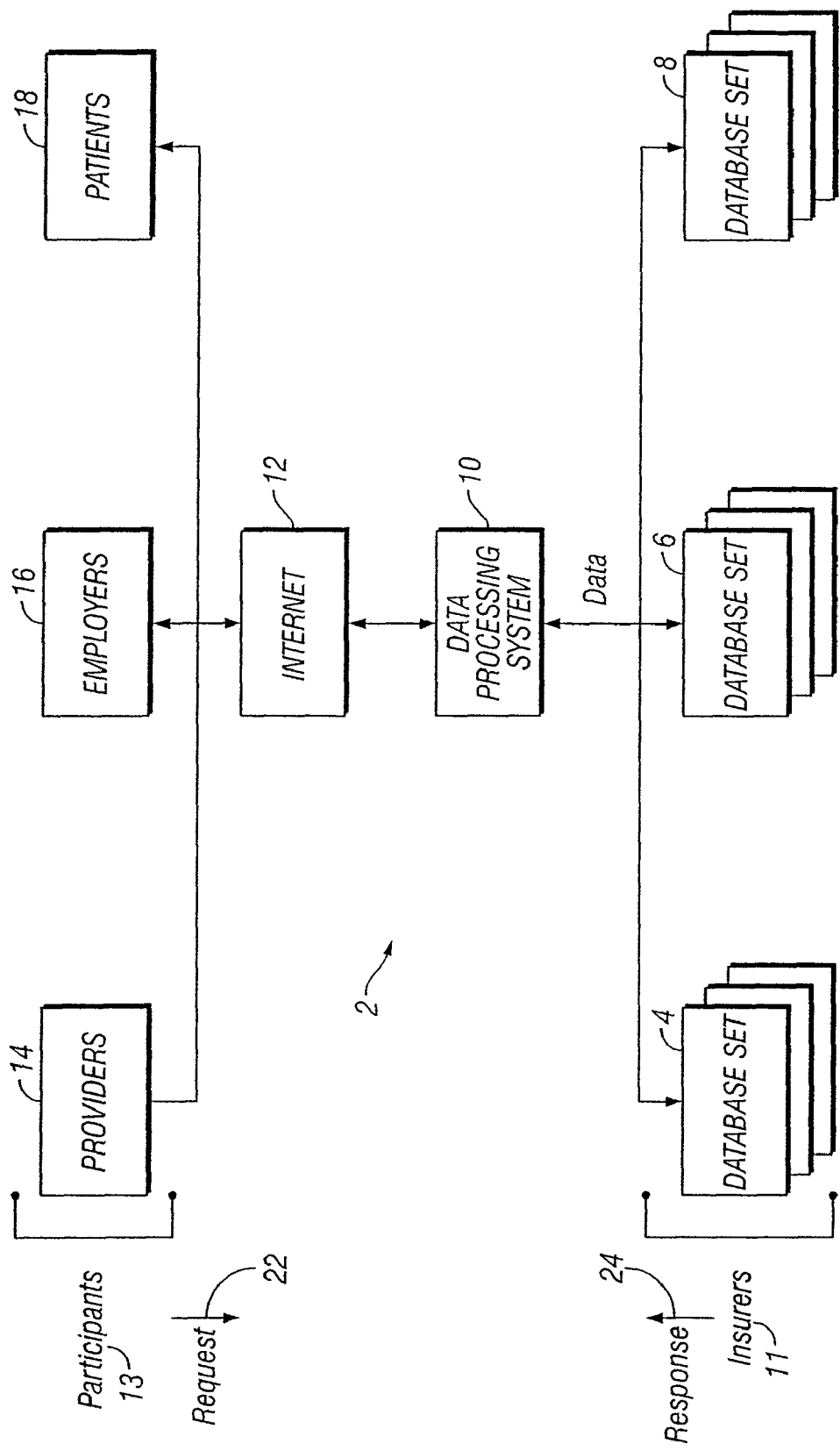
FIG. 1 is a diagrammatic view of a system for normalization of health care data and the exchange of same between several health care insurers and various health care participants.

An illustrative embodiment of the invention, such as that shown in FIG. 1, comprises a system 2 which includes a plurality of database sets 4, 6, 8 offered by a variety of insurers 11. It is appreciated that each health care database set 4, 6, and 8 represents an insurer's database processing system or series of processing systems and databases. For example, database sets 4, 6, or 8 may each represent a conventional computer system, a server, a local area network (LAN), a legacy, or other computer system storing one or more databases. It is contemplated that to transmit data, either the system as it exists is capable of doing so, or a system is added to either database sets 4, 6, or 8 to perform this function. It is further contemplated that each of database sets 4, 6, 8 may represent a single database or a plurality of databases, each of which may be of any variety of database formats or languages.

For the purposes of this application, it is contemplated that reference to the term "insurer," as used herein for insurers 11, is for illustrative purposes only. Such a term includes health insurance companies, but also includes health maintenance organizations, self-insured entities, disease management organizations, capitated health care providers, Medicare agencies, as well as any other organization that might store or manage health care data. The term "insurer" is not to be construed as being limited in scope to only health insurance companies or other "payors."

Conventionally, health care data is stored on an insurers' computer or series of computers in several databases, each of which often being in a unique format, with each database format being incompatible with other database formats. For example, one insurer may have their health care data stored in one format, and a second insurer may have their health care-related data stored in a second format that is not compatible with the one format. Additionally, and more problematic is that, even within the same insurer's 11 system, eligibility data, for example, may exist in a database of one particular format, developed to suit the needs of its users at the time, whereas, the claims data, for example, may be stored in another database in a format that suits the needs of those users, but with its format being incompatible with the format of the eligibility data. In either example, it is contemplated that in the present invention, health care data of any format is normalized into a common format, and distributed through a common network, like internet 12, to a health care participant 13, who uses the normalized data to conduct health care-related transactions and tasks. It is further contemplated, and to be discussed further herein, that various levels of access and security can be provided to assure that those participants 13 accessing the normalized data are authorized to access only that data predetermined as necessary and appropriate for their particular use or need.

As FIG. 1 shows, data from each database set 4, 6, 8 can be transmitted to a data processing system 10 that normalizes the data into a format readable by particular health care participants 13. More specifically, the data is transmitted over the internet 12, which is operatively connected to and read by participants' 13 computer(s) or terminal(s). Such participants 13 illustratively include providers 14, employers 16, and patients 18, or any combination thereof. It is contemplated that participants 13 can further include any other interested party that can request data or information from an insurer, including other insurers and disease management organizations, for example.

It is contemplated that the transmission of data from database sets 4, 6, or 8 is initiated by any of the participants 13 submitting a request 22 through a computer or computers. Request 22 is transmitted through the internet 12 to data processing system 10 which retrieves the appropriate data from the appropriate database set or sets of either 4, 6, or 8. That data is normalized to a common format, at which point a response 24 to the request 22 is made. For example, a health care provider 14 may place a request 22 on behalf of an insured to authorize payment for a medical procedure. In this example, it is presumed that the data required to formulate a response 24 exists collectively on eligibility, benefits, and claims databases that illustratively exist on database set 4. Data processing system 10, in order to prepare a response 24, determines and extracts which data is necessary from the databases. System 10 then normalizes the data into a homogenous format, and then determines what the nature of the response should be. In this example, response 24 should be to either authorize or deny payment for the medical procedure. System 10 uses the normalized data to determine the response, which is then transmitted to provider 14, thus, completing the transaction. It is contemplated that system 2 may comprise any number of insurers 11 or participants 13. Specifically, data processing system 10, as will be discussed further herein, is able to connect and manage transactions between a single or plurality of participants 13 with any insurer or plurality of insurers 11.

It is further contemplated that system 2 will provide health care participants 13 with a variety of health care transaction options referred to generally in the form of requests 22 and responses 24 between participants 13 and insurers 11. Examples of transactions available to health care providers 14 are: eligibility/benefit display, member roster, claim submission, provider lookup, formulary lookup, diagnosis code lookup, procedure code lookup, access health plan information online, communicate with a health plan on-line, communicate with patients on-line, patient-centric view of data across several health plans, order generation and tracking, results review and release, result printing, prescription writing, medication profile for each patient, access to patient's personal health record based on patient approval, personalized medical and health care content integration, both context-specific and on demand, e-commerce integration: office, medical and health-related product awareness and buying capabilities, email, practice management system subscription, support disease management, and physician credentialing subscription.

As further example, the following are specific records and fields for health care transactions between providers 14 and insurers 11 that utilize normalized data:

Record: Summary
    Fields:
  Activity for (date)
  Referrals
  Claims
  Test Results
  Members
  Update State for Americas Health
  Benefit Records
  Claim Records
  Patient Records
  Provider Records
  New Just For You Record: Eligibility
    Fields:
  Today's Patients
  Patient Search
  Sex
  Coordination of benefits
  Medicare data
  Add to patient list
  Name
  From Date
  To Date
  Birth date
  Member ID
  Relation
  PCP
  Address
  City
  State
  Zip
  Current Benefit
  Group
  Carrier
  Benefit Plan Record: Claim Status
    Fields:
  Patient Name
  From Date
  To Date
  Claim Number
  Status
  Provider Name
  Patient Name
  Member Number
  Billed Amount
  Patient Responsibility
  Paid Amount
  Date of Service Record: Claim Detail
    Fields:
  Member
  Provider
  Diagnosis
  Description
  Line number
  DOS
  CPT Description
Modifier
Location
Units
Status
Billed
Allowed
Copay
Coinsurance
Deductible
Paid
Totals
Record: Explanation of Payments
          Fields:
  Line Number
  Status Description
  Explanation
  Check/Date
Record: Select Specialist
          Fields:
  Address
  City, State, Zip
  Handicap Access
  Office Hours
  Contact
  Phone
  Fax Phone
  Phone After Hours
  Sex
  Birth Date
  Specialty
  Second Specialty
  Accept Patient
  Primary Care
  Board Cert
  Languages
  Hospitals
  Hospital Privileges
  Networks
Record: Add Claims
          Fields:
  Health Insurance
  Insured's ID Number
  Patient Last Name
  First Name
  Middle Name
  Patient's Address 1
  Address 2
  City
  State
  Zip
  Patient's Phone
  Birth date
  Gender
  Relationship to Insured
  Marital Status
  Patient Employment Status
  Condition Related to Job
  Con. Rel. to Auto Accident
  Cond. Rel. to Other Accident
  Insured's Last Name
  First Name
  Middle Name
  Gender
  Birth date
  Insured's Address 1
  Address 2
  City
  State
  Zip
  Phone
  Insured's Group or FECA Number
  Insured's Employer/School
  Insured's Insurance Name
  Referring Physician Name
  Referring Physician ID
  Outside lab
  Outside Lab Charges
  Medicaid Resub Code
  Medicaid Orig.
  Prior Auth. Number
  Diag Codes
  Item
  Date From
  Date To
  Place
  Type
  Procedure
  Mod 1
  Mod 2
  DX Ind.
  Charges
  Days/Units
  Patient
  Provider
  From Date
  To Date
  Diagnosis 1
  Diagnosis 2
  Diagnosis 3
  Diagnosis 4
  Procedure Line
  CPT
  Description
  Amount
  Dx pointer
  Other Errors
  Total Amount
  Billed
  Allowed Amount
  Copay Amount
  Withheld Amount
  Writeoff Amount
  Predicted Payment
Record: Referral Status
          Fields:
  Referral Number
  Patient (Member ID)
  Valid from (months)
  Referred by
  Referred to
  Patient List
  Referred by
  Referred to
  Referral Number
  Status
Record: Add Referrals
          Fields:
  Today's Patients
  Patient Search
  Specialists
  Specialist Search
  Providers
  Diagnosis Patient
Specialists
Provider
Diagnosis
Start Date
Months Valid
Visits Requested
Reason
Record: Procedure and Diagnosis Data
    _____Fields:
  Diag Number
  Diagnosis Name
  Proc Code
  Procedure Name
  Visits Allowed
  Patient
  Patient Search
  Referred to
  Specialist Search
  Referred by
  Diagnosis
  Start Date
  Exp Date
  Visits Requested
  Remarks
  Services Requested
  Authorized Ancillary Services
Record: Diagnosis Codes
    _____Fields:
  Diagnosis Code
  DX Code
  Diagnosis Code Description
Record: Procedure Codes
    _____Fields:
  Procedure Codes
  Procedure Code
  Procedure Description
  Age From
  Age To
  Sex
  Location Code
Record: Drug Therapeutic Class Listing
    _____Fields:
  Therapeutic Class
  Class Description
  Count of Drugs in this Class
Record: Formulary List by Therapeutic Class
    _____Fields:
  Drug Name
  Generic Name
  Drug Class
  Therapeutic Class
  NDC
Record: Write Prescription
    _____Fields:
  Today's Patients
  Patient Search
  Providers
  For
  Medication
  Dispense
  Refill
  Sig: Take
  Sig: For
  Instructions
  Select Pharmacy
Record: Medication Profile
    _____Fields:
  Type
  Medication
  Dose
  Frequency
  Reason
  Status
Record: Discontinued Medications
    _____Fields:
  Type
  Medication
  Dose
  Frequency
  Reason
  Status
Record: Allergies
    _____Allergen
  Reaction
  Date Started
Record: Medical Test Orders
    _____Fields:
  Patient ID
  Patient Name
  Provide ID
  Provider Name
  Location
  Lab Name
  Dx
  Action
  Battery
  Test
  ID
  Type
  Volume
  Date
  Time
  Collected By
  Chemistry
  Hematology
  Toxicology/Therapeutics
  Microbiology/Virology
  Immunology/Serology
  Urinalysis/Fluids
  Procedure
  When
  Priority
  Specimen
  Alert
Record: Results
    _____Fields:
  Status
  Order number
  Test Procedure
  Alert
  Order Date
  Facility
  Patient
  Provider
  Date/Time
  Procedure
  Status
  Indicator
  Date/Time
  Performed
  Specimen Number
  Type
  Status Result
Value
Desired Range Each field listed above represents data that can exist anywhere on database sets 4, 6, or 8, and be in any format or language. If any request 22 is made which calls up one or more of the above records, data processing system 10 searches, extracts, and normalizes the data so it appears in the correct field in the record. It is appreciated that provider 14 may change the data, if necessary, and transmit it back through interne 12 and data processing system 10 to be stored on the appropriate database set 4, 6, or 8.

Examples of transactions available to employers 16 are: group eligibility, group enrollment, enrollment changes, formulary lookup, e-commerce integration, access from health plan web site or direct access via URL, personalized content integration, both context-specific and on demand, e-commerce integration: human resource, business (e.g., office supplies) and health care-related product awareness and buying capabilities.

Again, as a further example, the following are specific records and fields for health care transactions between employers 16 and insurers 11 that utilize normalized data:

Record: Open Enrollment
_____Fields:
  Health Insurance
  Employer Group Number
  Last Name
  First Name
  Middle Name
  Employee Address 1
  Address 2
  City
  State
  Zip
  Home Phone
  Work Phone
  Primary Language
  Birth date
  Gender
  Social Security Number
  Primary Care Physician
  Established Patient
  Dependent Last Name
  First Name
  Middle Initial
  Birth date
  Gender
  Relationship
  Social Security Number
  Primary Care Physician
  Established Patient
  Effective Date
  Hire/Rehire Date
  Other Health Care Policy
  Name and Address of Insurer
  Effective date of other coverage
  Policy Holder's Last Name
  First Name
  Middle Name
  Policy/Group Number
  Covered by Medicare
  Medicare Number(s)
  Health insurance within the last 18 months
  If yes, type of coverage: group, individual, COBRA, Medicare/Champus, Conversion or Other
  Reason coverage was terminated
  Read and Agree to Authorization Statement Record: Enrollment—Changes
_____Fields:
  Health Insurance
  Employer Group Number
  Last Name
  First Name
  Middle Name
  Employee Address 1
  Address 2
  City
  State
  Zip
  Home Phone
  Work Phone
  Primary Language
  Birth date
  Gender
  Social Security Number
  Primary Care Physician
  Established Patient
  Term Member
  Dependent Last Name
  First Name
  Middle Initial
  Birth date
  Gender
  Relationship
  Social Security Number
  Primary Care Physician
  Term Dependent
  Hire/Rehire Date
  Effective Date
  Change Reason
  Name
  Enrollment Type
  Remarks Examples of transactions available to patients 18 are: identification card requests, address changes, provider directory inquiries, and personalized health information based on the member's interest profile, as well as diagnosis information from health plan administrative and clinical information, relevant articles and patient education materials, communications from health care providers and health care plans, lab and radiology results to patients online, scheduled appointments with a health care provider, referral status, prescription refills, education materials, personal health records so it can be maintained in his or her comprehensive health history online for physician reference, view eligibility/benefit information, view claim information, view referral and authorization information, provider lookup, personal health record, family history, medication profile, formulary lookup, and communications between member and provider.

Figure 2:
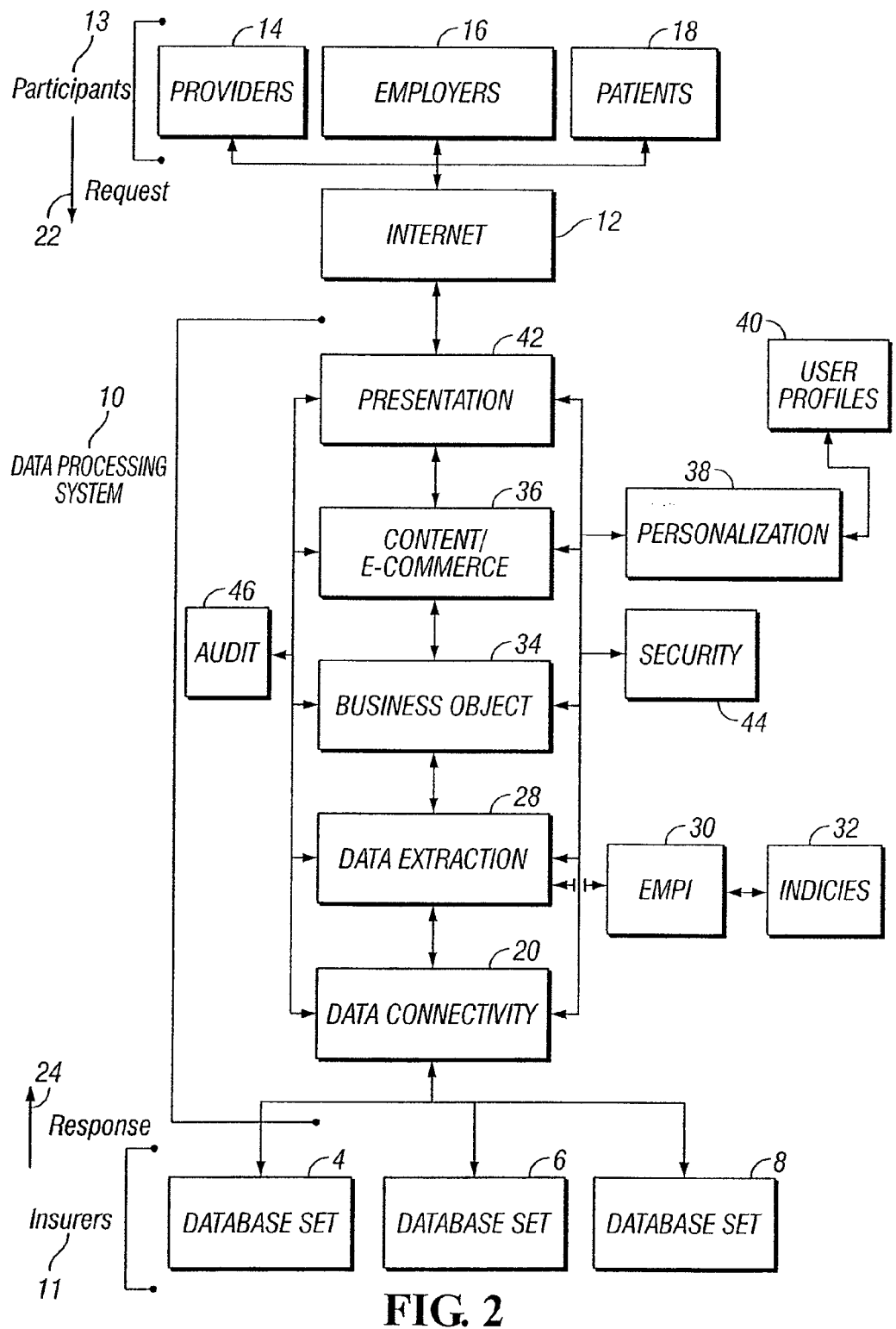
FIG. 2 is a diagrammatic view of the data processing system for the system of normalization shown in FIG. 1.

The architecture of the data processing system 10 is shown in FIG. 2. Each of the database sets 4, 6, 8 is operatively connected to data connectivity sub-system 20. The data connectivity sub-system 20 is configured to receive the different types of connections used between the various computer systems which store the database sets 4, 6, 8. It is appreciated that, in other embodiments, a separate data processing system 10 may be provided at the site of each of the database sets 4, 6, 8 such that each data processing system 10 is dedicated to manage and normalize the data, as discussed further herein, as well as manage server-to-server communications for a single database set.

The data extraction sub-system 28 is also depicted in FIG. 2. Sub-system 28 manages the integration of the often plurality of databases. The data extraction sub-system 28, as further discussed in reference to FIG. 3, also includes logic to manage data access from the several databases of database sets 4, 6, 8. An enterprise master person index ("EMPI") 30 is operatively coupled to data extraction sub-system 28. The EMPI 30 presents a cross-database view of all the insureds within system 2. It also manages the proper identification of providers 14, employers 16, connected patients 18, as well as other entities having unique identities on an as-needed basis. An indices database 32 is supported by EMPI 30. Specifically, the indices database 32 stores indices which serve as a basis for relating the identification data to each other. The indices database 32 is typically built upon and maintained by the EMPI 30.

The business object sub-system 34 contains the logic rules that drive the normalization of data and use of same between insurers 11 and participants 13. To provide such capabilities, a variety of processes may be supported in any particular situation. Illustratively, such processes may include, but are not limited to, rules-based evaluation of entered data for referral authorizations and admission pre-certifications; proxy or actual adjudication of claims submitted by providers, with concomitant delivery of funds to insurers 11 and benefits explanations to patients 18; sorted lists of providers 14, employers 16, and patients 18; and graphical displays of laboratory results and integrated claims-driven health records for patients 18.

The content/e-commerce sub-system 36 adds third party capabilities to the data processing system 10. The content portion of sub-system 36 provides management and integration of third party affiliated content, such as articles about diseases, bulletins, notices, notes, and other medically-related references. The e-commerce portion of sub-system 36 integrates e-commerce capabilities, including business-to-business or business-to-consumer purchasing through shopping cart-type databases with affiliated product and service vendors.

The personalization sub-system 38 integrates information from the previous sub-systems 20, 28, 34, 36 to provide a personalized view of data in system 2. Specifically, when any of the participants 13 login to system 2 and access data or other information from database sets 4, 6, or 8, or even the content/e-commerce sub-system 36, pertinent information derived from the type of content viewed, as well as the products purchased or searched, is maintained in a user profile database 40. During subsequent logins, therefore, the information a particular user views can be arranged and accessed in a more familiar, relevant, and useful manner, individual to that participant.

The presentation sub-system 42 manages the normalized data and information into a presentable format for participants 13. For example, the world-wide-web, being a popular destination for users of the internet, accepts output in HTML format, and is accessible by a conventional internet browser. It is appreciated, however, that such data may be presented in virtually any form to accommodate different access devices (for example, WAP for mobile devices).

A security sub-system 44 is shown in FIG. 2 integrated with the other sub-systems 20, 28, 34, 36, 38, 42. Security sub-system 44 maintains data security in several ways. First, one embodiment contemplates that the insurers' 11 data is maintained on its own on-site database, and is controlled by the insurers 11. Second, the insurers' 11 data is encrypted when it is routed from the insurers' 11 database to the connectivity sub-system 20 and, ultimately, the participants 13 when a request 22 is made. Third, the participants' 13 browser includes encryption to view or send data over the internet 12.

Finally, internal security is built into the data processing system 10 to only allow users with need-to-know access to particular data, such as claims and referral information. For example, providers 14 may have access only to claims and referral information of their insurers, but not individual claim summaries of their patients. Similarly, the employers 16 may have access to only their employees' claims information, but not some personal information.

An example of an encryption method is the 128 bit Secure Sockets Layer (SSL) with a key certified by VeriSign, Inc. Such SSL encryption means that data traveling through the internet and to participants' 13 browser cannot be interpreted by anyone between those two locations. Encryption is also useful because of the storage of user passwords. There is no place that a user's password is saved or used by the system as traditional cleartext. From one of the participants' 13 browser through internet 12 and to one of the insurers' 11 computer or server, the password is protected by SSL. Once the password reaches the final destined server, a cryptographic algorithm converts the password to a protected format. No one, therefore, who has privileged access to the server or any of the back-end applications, can get any user passwords.

In addition, encryption is useful along the operative connection to an insurer's 11 database sets 4, 6, or 8 to the data processing system 10. It is contemplated, however, that insurers' 11 computers or servers (database sets 4, 6, or 8) may not need such encryption along this operative connection, if the connection is a true point-to-point connection. Also, this encryption can be implemented through hardware or software, a virtual private network (VPN), or through the use of encryption protocols in a database, for example.

There are several modes with which data can be restricted, even within and among the insurers 11 and participants 13 of system 2. For example, security sub-system 44 may restrict the actual data that a participant 13 may request or view from any of insurers 11. A health care organization, thus, may only view data that they have provided. For example, doctors may only view claim data for their own patients. Alternatively, security sub-system 44 may restrict access to participants 13 to allow access to only particular fields on a particular screen of any particular database. For example, if a screen listed dollar amounts for claims, employers may wish to restrict who is able to view those dollar amounts. Other users, therefore, like patients 18, might be able to see the rest of the claims, but not the dollar amounts. Still, further, security sub-system 44 may restrict which screens will be accessible to which users. This level of security defines which functionality is available to the user. For example, a patient 18 in system 2 may not be able to view the claim submittal screen submitted by provider 14 at all, but may view a diagnosis information or health plan administrative screen. Customizable security based on the interests of the user may be included as well. This security method allows either the insurers 11 or participants 13 to set the parameters of security for the examples described above. It is further contemplated that this tool may be an internet-based tool that could add logins to the system, as well as specify values and screens that a particular user has access to. It is still further contemplated that a portion or all of the security measures can be employed throughout data processing system 12.

An audit sub-system 46, like security sub-system 44, shown in FIG. 2, is also integrated with the other sub-systems 20, 28, 34, 36, 38, 42. Audit sub-system 46 tracks the operation of all sub-systems. The information generated from audit sub-system 46 allows an administrator to monitor the operation of system 2 for problems and marketing trends.

Figure 3:
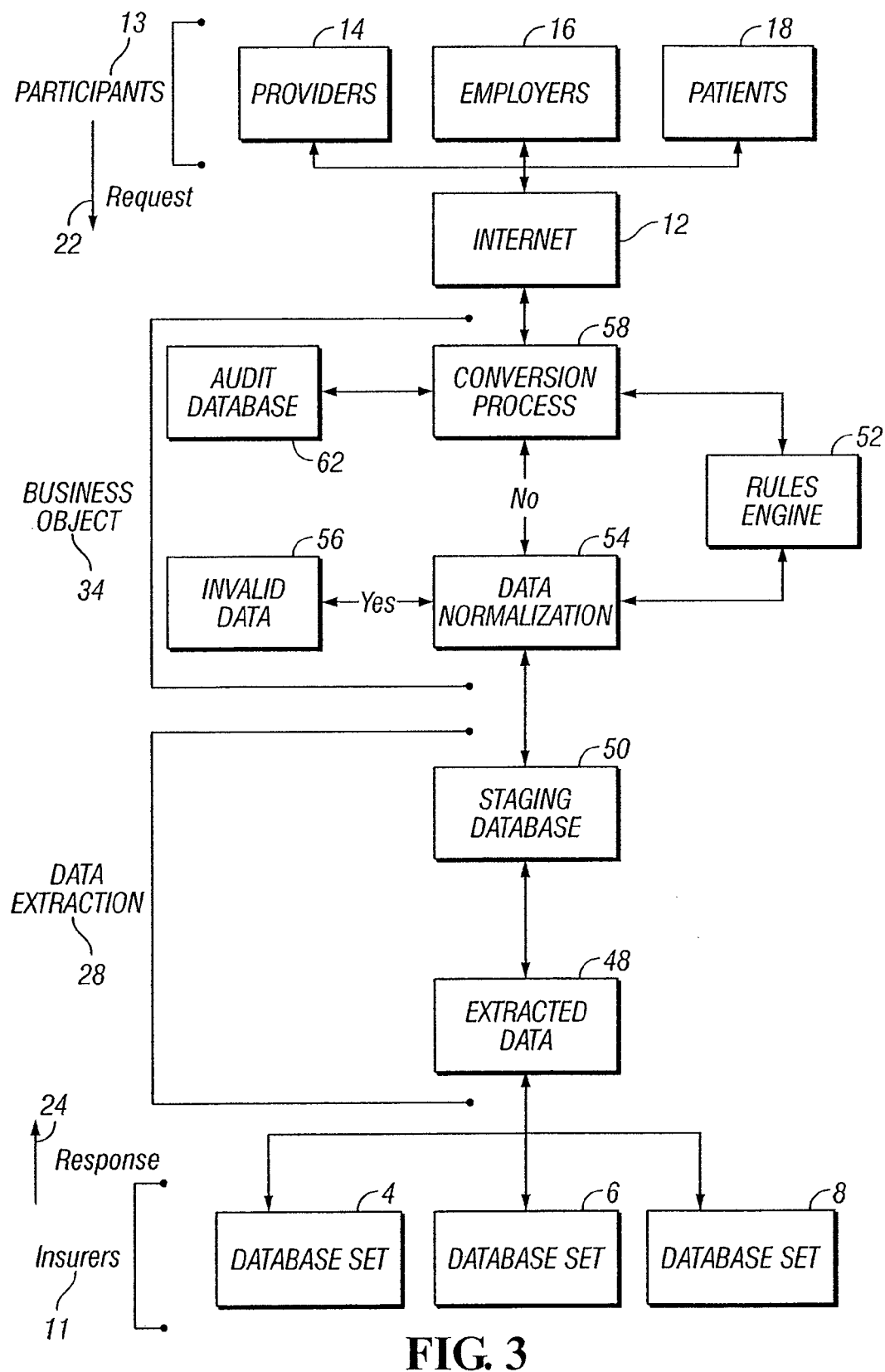
FIG. 3 is a diagrammatic view of the data extraction and business object sub-systems for the system of normalization shown in FIG. 1.

A diagrammatic view of the data extraction and business object sub-systems 28, 34, respectively, is shown in FIG. 3. As previously discussed, the numerous databases represented by database sets 4, 6, 8 contain data in a variety of formats. Before the data is transferred to one of the participants 13, however, it is first formatted to a new format that is readable by any of the computers of participants 13, like HTML format, for example. The data is, therefore, "extracted" from the database sets, either 4, 6, or 8, and then "normalized" to be read by the computers of participants 13. The extracted data is indicated by reference numeral 48.

Extracted data 48 from either database sets 4, 6, or 8 is uploaded to a staging database 50 which is typically a portion of data extraction sub-system 28. Rules engine 52 serves a dual purpose of defining the rules that control the normalization of the data, as well as how the data, once normalized, is used. During the normalization process at 54, rules engine 52 homogenizes the data by determining what the data means, then inserting the data into the proper field as normalized data. Rules engine 52 also remodels the data, if necessary, to a structure or appearance predefined by the normalized format. As a simple example, in a referrals database that may hypothetically exist on database set 6, it may include the entry "New Jersey" in the state location field. If that field is requested by a participant 13, the rules engine 52 will cause that field to be extracted, then determine whether the meaning of this field corresponds to the meaning of the normalized state location field, and, if so, then convert the field to the normalized state location field at 58. Furthermore, if the rules engine 52 has predetermined that the normalized state location field should exist as only a two-character acronym, then the phrase "New Jersey" will be remodeled to the acronym "NJ." This is contrasted with traditional transliterating programs that would merely match the state location field of the referrals database with any field in another database titled "state location field" and then transfer the data. Such a program cannot determine the meanings of the state location fields, and then determine if their meanings matched, as well as not remodel the data to the appropriate appearance. For example, a field for laboratory enzymes might be expressed in Celsius in one database and in Fahrenheit in another database. Such data, as well as countless other data, are typically contextualized by the system they exist in. Transliterating programs do not compensate for such context among data. In the present disclosure, part of the normalization is determining the meaning of the data and locating it in a field of the same definition, but in a single format.

Rules engine 52 also determines whether the data is bad or invalid. Any bad or invalid data that is discovered during the normalization process at 54 is transferred to an invalid data database 56. Invalid data is placed in database 56 for review and appropriate corrective action and, if appropriate, reintroduced and normalized.

In addition, the rules engine 52 incorporates security 44 to determine whether the requestor has authorization to view the data that is being requested, as previously discussed. For example, if employer 16 requests claims data that illustratively exists on database set 8, the rules engine 52, in conjunction with the security 44, determines whether employer 16 has authorization to view the data subject of that request. If not, rules engine 52 would deny fulfillment of the request.

Once the data is converted and remodeled into the normalized format, rules engine 52 determines how the normalized data can be used. For example, if a request 22 is made from providers 14 to one of the insurers 11 to authorize a chest X-ray for one of the patients 18, a proper response 24 may reference data from various eligibility, claims, benefits, and personal data databases which rules engine 52 first extracts and normalizes. Once the data is normalized, rules engine 52 undertakes the process of responding to request 22. Rules engine 52 bases response 24 on predetermined rules established by the particular insurer 11 to determine whether a chest x-ray is an approved procedure in response to the request. It is contemplated that each insurer 11, or even each database set 4, 6, 8 can be subject to its own unique set of rules to govern any particular response 24.

An audit database 62, illustrated in FIG. 3, manages and maintains tracking information during the conversion process at 58. All data requests, responses, and e-commerce submissions can be monitored and recorded. This audit trail information is maintained in audit database 62 to enhance performance and security characteristics. It is contemplated that audit database 62 can be integrated with audit sub-system 46, as shown in FIG. 2, or database 62 can be a stand-alone system working independently or in addition to sub-system 46.

Figure 4:
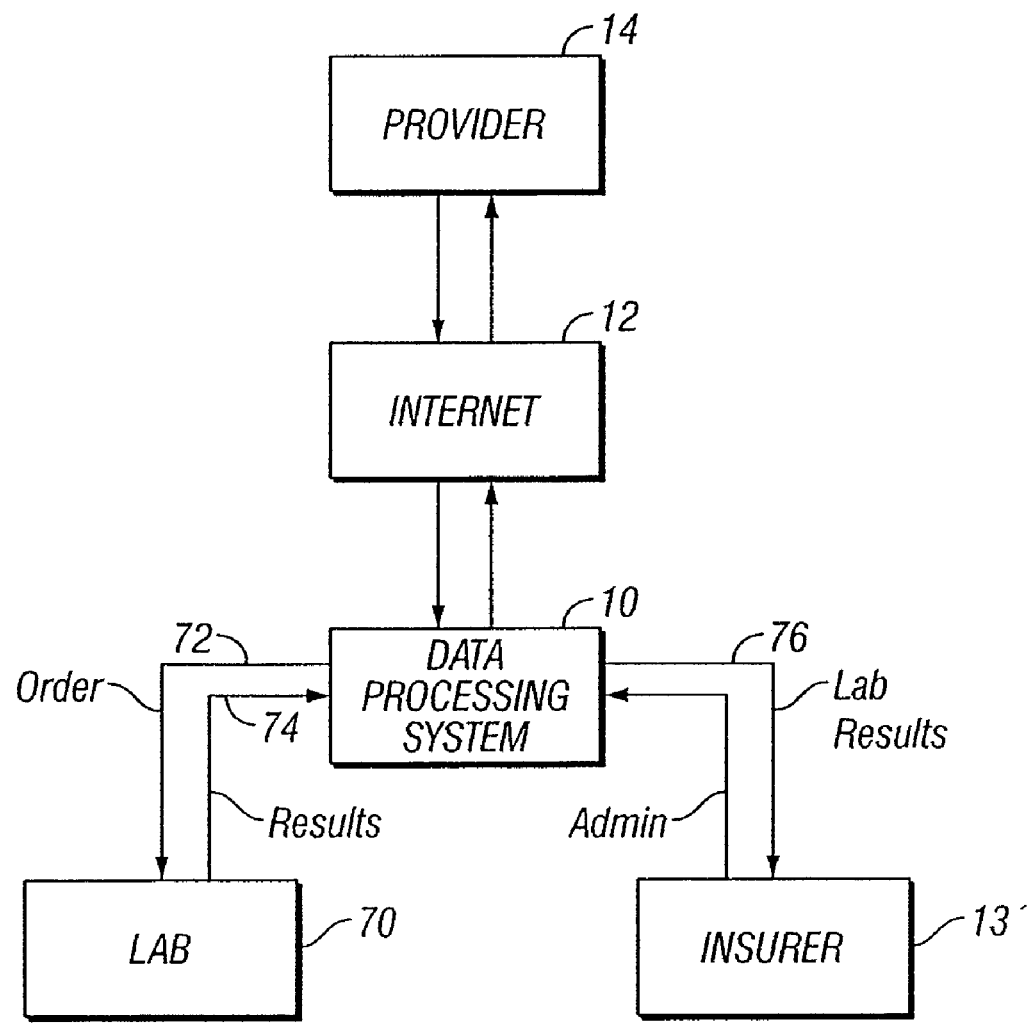
FIG. 4 is a diagrammatic view of a system of health care management for medical testing between health care insurers and participants.

In one embodiment of the disclosure, it is contemplated that system 2 will not only exchange information related to insurance and payment issues, but also provide active management of patient care. For example, as shown in FIG. 4, a portion of system 2 depicts the process for medical tests to be ordered, approved, and results submitted. For example, a health care provider 14, via the internet 12, places an order for a medical test. The order is transmitted through data processing system 10. The order is further transmitted at 72 to a laboratory 70, the order will disclose particular information that will be needed when either the specimen or the patient arrives. If a specimen is collected by provider 14, the order will identify the laboratory 70, and provide information to provider 14 so that the specimen may be marked accordingly before being sent to laboratory 70. Once laboratory 70 receives the order and the specimen, laboratory 70 can either communicate the status or results back through data processing system 10 to both the provider 14 and the appropriate insurer 13', as indicated by reference numerals 74, 76, respectfully.

Figure 5:
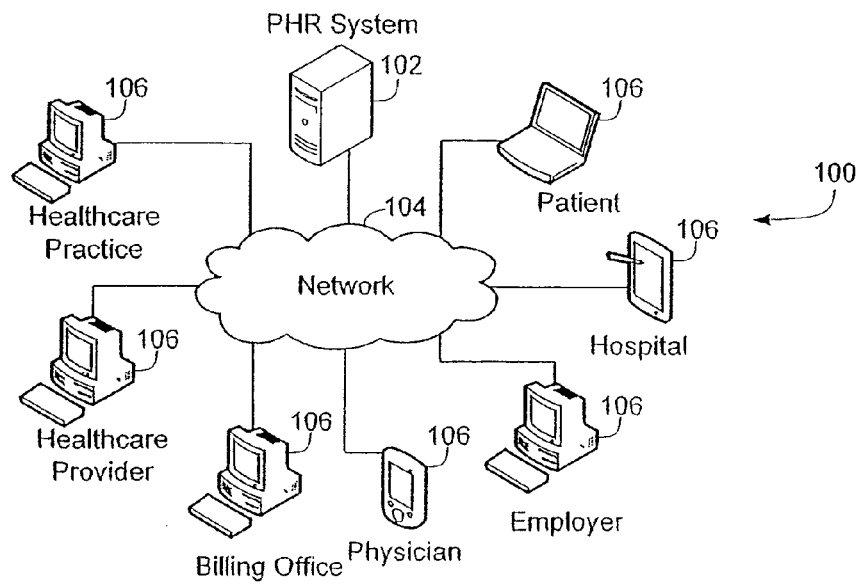
FIG. 5 shows a diagrammatic representation of a health care data system according to an embodiment of the present invention.

FIG. 5 shows a health care data system 100 in accordance with one illustrative embodiment that may be used to build, access, analyze, and/or update a Personal Health Record, also described as an Electronic Health Record or Individual Health Record (hereafter the terms "PHR" and "EHR" and "IHR" are intended to convey the same meaning). As shown, the health care data system 100 includes a personal health record system 102 ("PHR System") that is configured to provide access to individual health records via a network 104 to one or more client systems or users 106. The PHR system 102 may take the form of hardware, software, or may combine aspects of hardware and software. Although the PHR system 102 is represented by a single computing device in FIG. 1 for purposes of example, the operation of the PHR system 102 may be distributed among a plurality of computing devices. For example, it should be appreciated that various subsystems (or portions of subsystems) of the PHR system 102 may operate on different computing devices. In some such embodiments, the various subsystems of the PHR system 102 may communicate over the network 104.

The network 104 may be any type of communication scheme that allows computing devices to share and/or transfer data. For example, the network 104 may include fiber optic, wired, and/or wireless communication capability in any of a plurality of protocols, such as TCP/IP, Ethernet, WAP, IEEE 802.11, or any other protocol. Embodiments are contemplated in which the PHR system 102 may be accessible through a shared public infrastructure, such as the Internet. In such embodiments, any data transmitted over the shared public infrastructure is preferably encrypted, such as by using a public key infrastructure ("PKI") certificate and/or secure sockets layer ("SSL"). In some exemplary embodiments, a virtual private network ("VPN") may be used. Those skilled in the art should appreciate that various other security measures could be employed in relation to transmitting data over the network 104.

The client systems (or users) 106 may be any form of computing devices that can receive and send digital signals. By way of example, the client systems 106 may include personal computers ("PCs"), tablet computers, notebook computers, servers, personal digital assistants ("PDAs"), or cellular phones. The client system 106 shown in FIG. 1 includes labels indicative of typical users of the PHR system 102. For example, embodiments are contemplated in which patients, hospitals, employers, physicians, billing offices, healthcare providers and/or healthcare practices may access the PHR system 102. However, the client system's labels shown in FIG. 5 are provided solely for purposes of example, but are not intended to limit the type of users or require particular users to connect to the PHR system 10.

Figure 6:
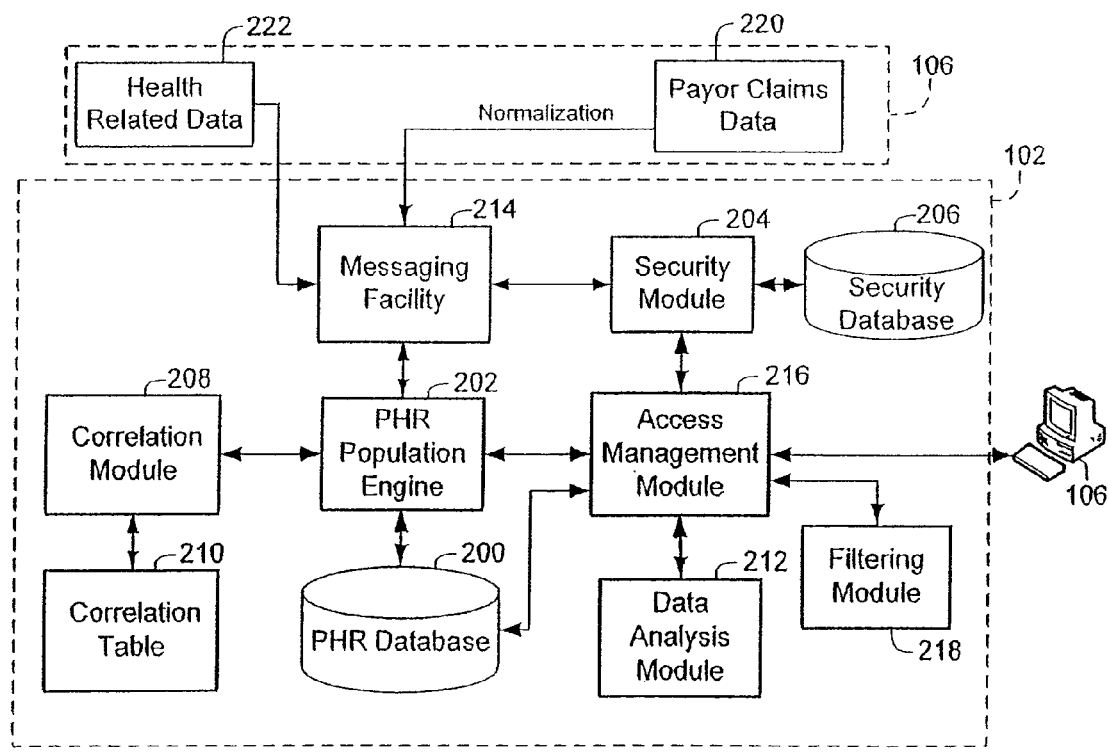
FIG. 6 shows a block diagram of an example PHR system according to an embodiment of the present invention.
Figure 8A:
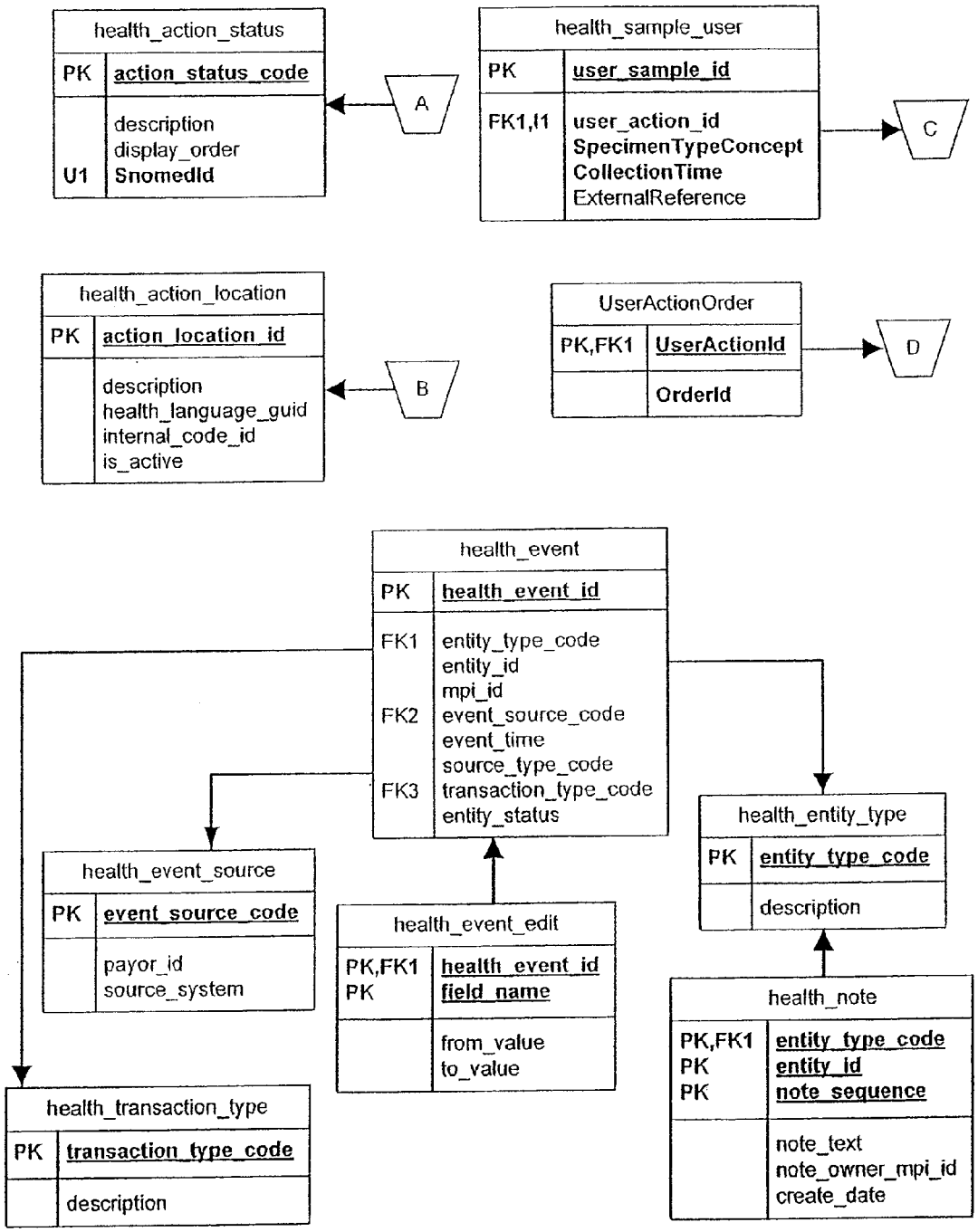
Figure 8B:
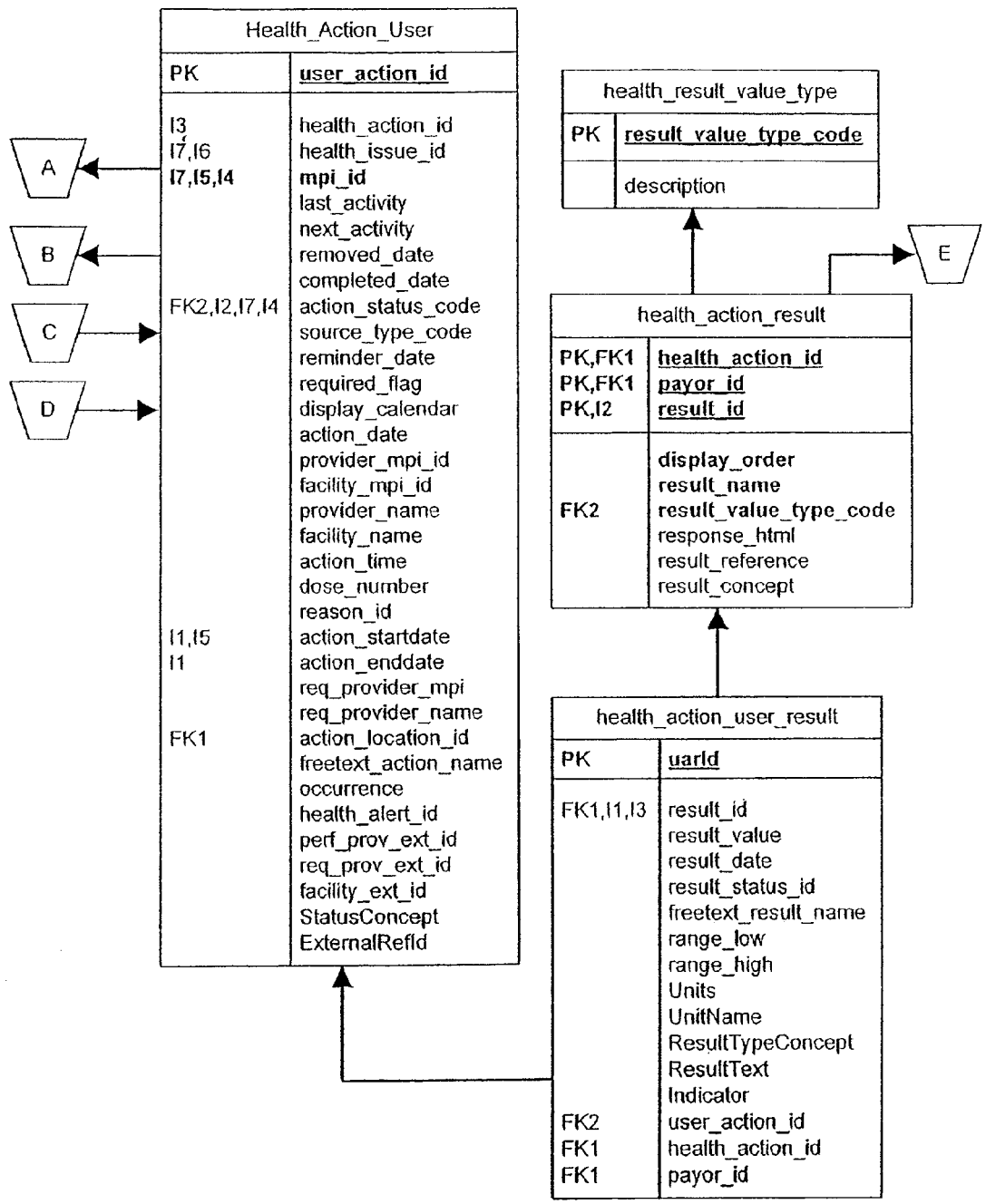
Figure 8C:
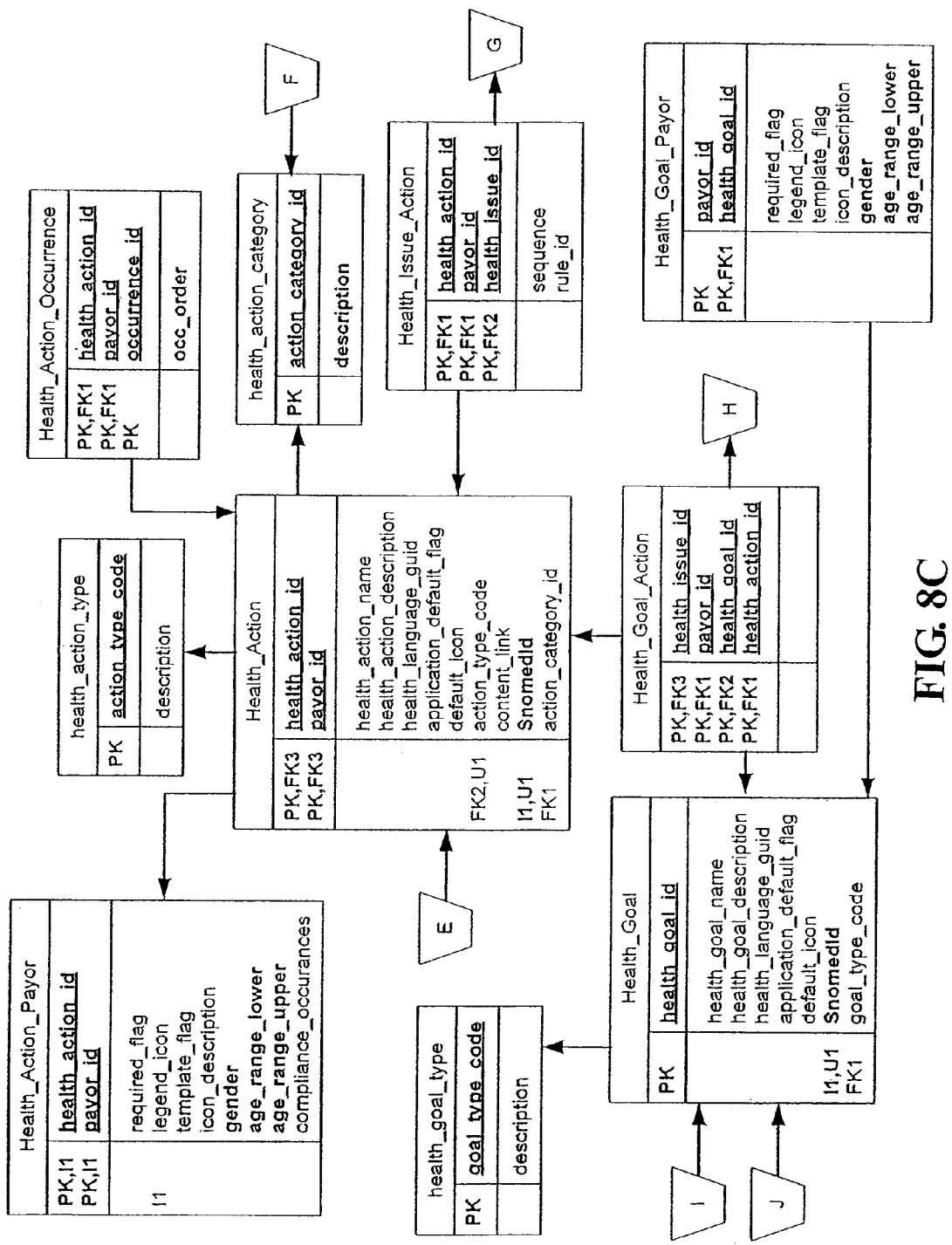
Figure 8D:
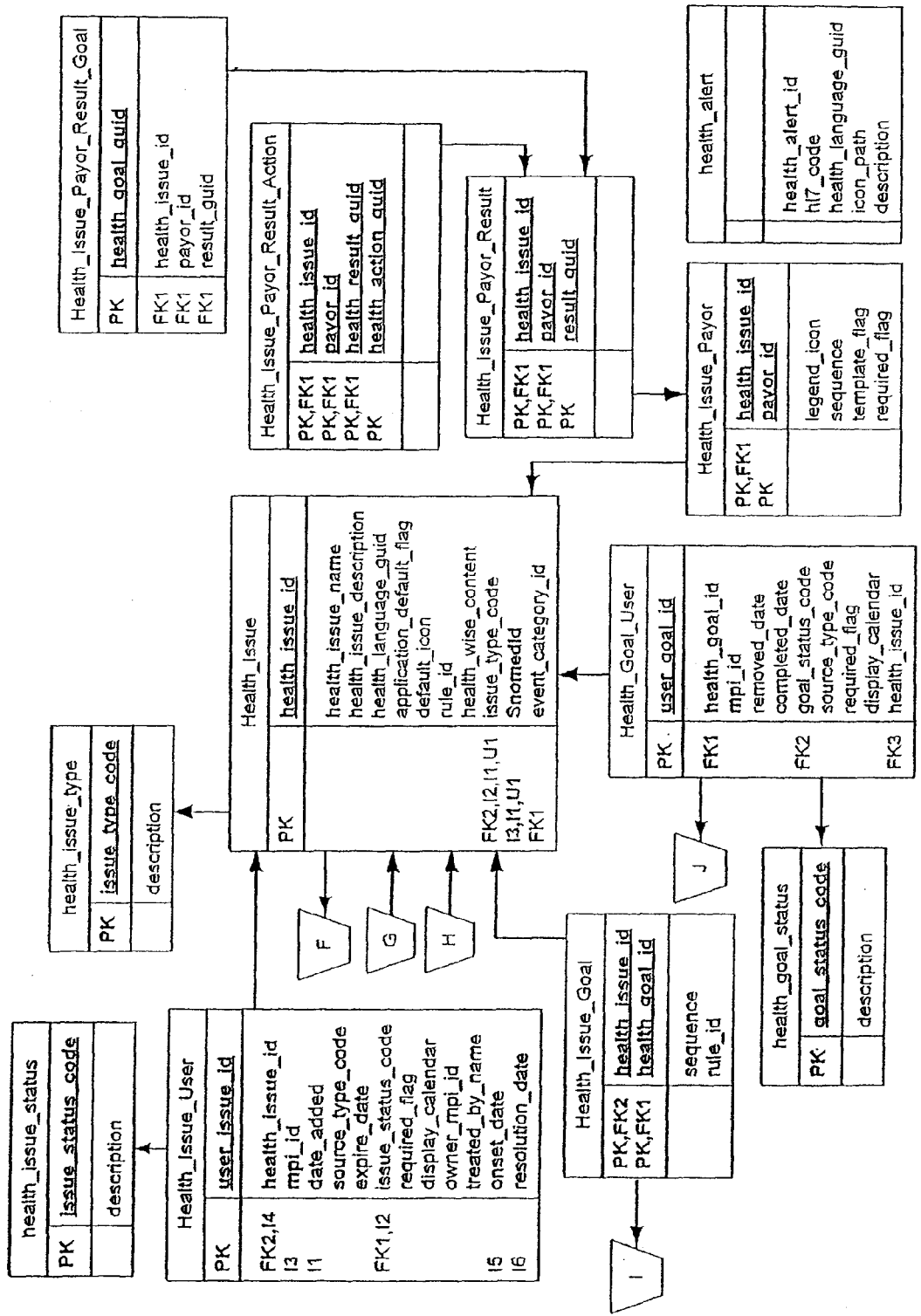

FIG. 6 shows an example embodiment of the PHR system 102. In the embodiment shown, the PHR system 102 includes a PHR database 200, a PHR population engine 202, a security module 204, a security database 206, a correlation module 208, a correlation table 210, a data analysis module 212, messaging facility 214, an access management module 216, and a filtering module 218. Embodiments are also contemplated in which one or more of these subsystems of the PHR system 102 are optional, but may merely be "nice to have" depending upon the exigencies of a particular situation. For example, the data analysis module 212 may be optional in some embodiments. By way of another example, the filtering module 218 may be optional in some embodiments. As shown, the PHR system 102 has access to payor claims data 220 and health related data 222. In some embodiments, the payor claims data 220 and the health related data 222 may be accessible to the PHR system 102 via the network 104 from the client systems 106.

The PHR database 200 may be structured to store various data relating to the health care of patients, including individual health records. Preferably, the PHR database 200 includes a plurality of PHRs for a plurality of patients. Typically, the PHR database 200 may include ten thousand to sixty million or more PHRs. Embodiments are contemplated in which the PHR database 200 may be a single database or a plurality of databases, each of which may be of any variety of database formats or languages. It should be appreciated that the PHR database 200 may be a logical dataset that may physically reside on a single storage medium or multiple storage media. In some cases, for example, the PHR database 200 may be a logical dataset that physically resides in multiple geographic locations.

In some embodiments, the PHR database 200 may include a master patient index ("MPI") field. The MPI field allows for the assignment of a unique identifier that defines an entity, such as a patient. Due to the massive amount of PHRs contemplated in the PHR database 200, many of the patients may have the same name. Consider, for example, a PHR database 200 that includes twenty million PHRs. In this example, there may be thousands of patients with the last name of "Smith" and numerous persons with the name "John Smith." Although the use of the MPI will differentiate the persons, the assignment of an MPI to a patient may include other criteria that may be unique to a patient. In some embodiments, for example, various other criteria, other than name, may be used to determine whether an entity has already been assigned an MPI, before an MPI is assigned. For example, the PHR system 102 may determine whether various data elements already exist in the PHR database 200 before assigning an MPI, including but not limited to tax IDs, birthdates, gender, address, etc. If the entity is determined to already exist, the information is applied to an existing PHR. Otherwise, a new PHR is created and a new MPI is assigned.

The MPI could be used to secure data, store patient specific settings, and/or act as a key when requesting health record data, for example. The MPI could also create a cross reference to identifiers already being used across different information systems of various health organizations. For example, hospitals, lab systems, provider offices, pharmacy benefits managers, health plans and/or other systems may be cross-referenced to the MPI, thereby tying all relevant data to an appropriate patient. By way of another example, the MPI allows a central patient search that would allow users to find patients across multiple, massive and discrete health related organizations without requiring a national ID number. In some organizations, for example, there may be data on fifteen million to twenty million patients. The use of the MPI also allows data collected from various sources to be aggregated into a single record {i.e., a single PHR with data collected from a plurality of sources}.

FIG. 7 is an example use of the MPI with respect to a patient identified as "Ann Smith." In this example, Ms. Smith has been treated by or visited the six listed healthcare organizations. Each of these organizations has assigned their own identifier for Ms. Smith shown by the system identifier column, while the MPI identifier remains a single unique tracking mechanism. In some embodiments, the MPI could not only generate a unique identifier for Ms. Smith, but could also cross reference information to the system identifier used by each of the organizations. In this manner, Ms. Smith's identification could be picked up when another message from the same system is received. This allows the matching of information originating from a wide range of medical sources and from multiple payors to a single comprehensive display about a patient. In some embodiments, the MPI could also be used to tie health information related to a patient and their family members. For example, the presentation of information regarding the patient and their family could be available in formats that assist both the health care provider and the patient in improving their health care.

FIGS. 8A-8D shows a diagram of an example relational database which could be used as the PHR database 200 in some illustrative embodiments. It should be appreciated that the database structure shown in FIG. 8 is for purposes of example only, but that a multiplicity of database structures could be used for the PHR database 200.

The PHR system 102 may include a PHR population engine 202 to populate and/or update the PHRs in the PHR database 200. The PHR population engine 202 may collect data from a wide variety of sources, such as medical claims, pharmacy claims, orders and results from laboratory systems, admission summaries, op report and discharge summaries from custom and standard hospital interfaces, and manually entered information from surveys, health risk assessments and direct entry. In some cases, manually entered data may be inputted by the patients themselves or representative from health plans, provider offices, hospitals, etc. By populating the PHRs from a variety of sources, the PHRs would not be limited to the data available from individual practices and hospitals. The table below shows a variety of sources from which the PHR may be populated, according to one embodiment, along with example information that may be gleaned from each source:

| SOURCE | METHOD OF COLLECTION |
|---|---|
| 1. Patients | Answers to questionnaires and surveys. Regular entries pertaining to management of their conditions, such as home blood glucose levels, airway test results, etc., to track the progress of the disease condition. Patients may also directly enter information, such as over the counter drugs, immunizations and allergies, into their PHR directly by connecting to the PHR system. |
| 2. Health Plans | Directly collecting the claims data from the claim processing systems on a periodic (e.g., daily basis) or real time basis. Deriving the data to obtain clinical information. This information may also be entered directly into PHRs by persons associated with the health plans, such as case and disease managers. |
| 3. Pharmacy Benefits Manager ("PBM") | Electronic tape or direct access to obtain data relating to prescriptions. |
| 4. Labs | From the lab systems using Universal interfaces (e.g. HL7) or customized interfaces. |
| 5. Imaging Centers | From the Imaging Center Systems using Universal (HL7) or customized interfaces. |
| 6. Freestanding Outpatient Facilities | From the EMR of the facility using Universal or customized interfaces. |
| 7. Hospitals | Information imported from the respective EMR's of the hospital using Universal Interfaces (such ass HL7) or customized interfaces. |
| 8. Physicians | a. From the claims submitted to the payers<br>b. direct online notes or input to the PHR |

Embodiments are contemplated in which the PHR population engine 202 may "pull" data from various sources. In some embodiments, for example, a "flag" or other notification could be sent to the PHR population engine 202 that health related data is ready to be updated. It should also be appreciated that various health related organizations could "push" data to the PHR population engine 202. For example, the client systems 106 may access the PHR system 102 to update the PHR of a patient in the PHR database 200. In other embodiments, the PHR population engine 202 may periodically receive data from various sources. For example, the PHR population engine 202 may download payor claims data (or other health related information) from an insurance company (or other payor or health provider) on a daily, weekly or other periodic basis. Embodiments are contemplated in which the PHR population engine 202 may download payor claims data or other health related data on a "real time" basis. The term "real time" does not necessarily mean instantaneous, but merely means that the PHR population engine 202 would update the PHR database 200 with new information before the information would be needed by a health care provider. For example, consider a patient that is referred to a specialist based on a visit with his/her primary care physician. In this example, the PHR population engine 202 would be considered to update the patient's PHR on a "real time" basis if the PHR is updated with information from the visit with the primary care physician prior to the visit with the specialist, whether the appointment with the specialist is scheduled the same day as the visit to the primary care physician, the next day, a week later, etc.

In some embodiments, the PHR system 102 may include a messaging facility 214 to interact with the PHR population engine 202 in handling messages that are received from various sources, such as client systems 106. In some cases, the messaging facility 214 may also generate response messages for client systems 106 that can programmically request an electronic copy of the PHR. Embodiments are contemplated in which programmical requests for portions of the PHR may be denied based on permissions associated with the PHR, as described below with respect to the security module 204.

Preferably, the messaging facility 214 is configured to handle messages 20 in a variety of different formats, both standardized formats, and custom formats. The message formats described herein are provided merely for purposes of example; however, it should be appreciated that the messaging facility 214 is not limited to the formats specifically described herein. By way of example, the messaging facility 214 may be capable of handling messages in HL7v2.4 and HL7v2.5 formats. These message formats include support for various health related information, such as hospital admission and discharge summaries, lab orders, radiology orders, radiology results and lab results. By way of another example, the messaging facility 214 may include support for HL7v3 format.

Embodiments are contemplated in which the messaging facility 214 includes support for ANSI-X12 837. This message format is defined by the American National Standards committee and imposed by the Health Insurance Portability and Accountability Act ("HIPAA") as the currently required standard for passing health care claims data between organizations. This message format includes a wealth of clinical information, including diagnosis and procedure codes, provider specialty data, treatment dates and many others.

The messaging facility 214 may also include support for NCPDP 5.1 format. This standard for passing prescription and medication information between entities was defined by the National Council for Prescription Drug Programs organization, and has been adopted by HIPAA as a pharmacy batch standard. While this message could be sourced from many locations, it would most likely be delivered from a Pharmacy Benefits Manager ("PBM"). The PBM may be within a health insurance plan, or operate as an individual entity, for example.

In some embodiments, the messaging facility 214 may receive messages over a secure connection to a web service. In some embodiments, the messaging facility 214 may include a certification mechanism to ensure that the organization is eligible to submit and request information from the PHR system 102. For example, each participating entity may be issued a Public Key Infrastructure ("PKI") certificate that will allow verification that only authentic messages are passed to the PHR system 102. The messages may be sent on a real-time basis from some organizations, typically hospitals and laboratories, but may be sent on a periodic basis from other organizations, such as health insurance plans and PBMs.

In some embodiments, the PHR population engine 202 may have access to payor claims data 220. The term "payor claims data" is intended to be broadly interpreted to include any patient related data associated with the payment of health related services. Typically, payor claims data 220 may be available from (or sent to) payors(s). As used herein, the terms "payor" and "payors" means health insurance plans and/or governmental bodies that pay for health related services, and/or pharmacy benefit managers. For example, the payor claims data 220 may include, but are not limited to International Classification of Diseases ("ICD") codes, Current Procedural Terminology ("CPT") codes, National Drug Code ("NDC")

codes, treating physicians, treatment dates, manually entered data, or other data formats. A wide variety of information may be obtained through the payor claims data 220. An illustrative example of information that could be collected for a PHR from the payor claims data 220 is provided below:

General Information
Age.
Sex.
Outpatient Encounter History
Vaccination history.
Mammography in women; retinal examinations for diabetics;
colonoscopy for adults; PSA tests for males; etc.
Visits to primary care doctor. Dates, duration, frequency, main diagnosis at each visit, medication prescribed following each visit, tests ordered with each visit, changes of medication as a result of each visit, changes in the frequency of visits to the PCP, changing diagnoses following visits.
Referrals or orders for lab tests and imaging tests with the diagnosis justifying the tests. Subsequent visit history to specialists, further tests and admissions to hospitals.
Referrals and visits to specialists. Diagnoses by specialists, lab tests and imaging tests ordered by specialists and diagnoses justifying tests.
Medications prescribed by specialists, with diagnoses. Duration of medication.
Multiple same-condition specialists, or physicians for the same diagnoses.
Medication to medication alerts generated. Medication-clinical condition adverse reaction alerts generated.
Psychotherapy/Psychiatric Therapy—dates, name of caregiver, diagnoses, medication.
Hospital Outpatient Encounter History
Tests done at the out patient facility—dates, tests and diagnoses. Any repeats?
Out-patient surgery—date of surgery, type of surgery, diagnoses for surgery, name of surgeon, name of anesthesiologist, complications.
Hospitalizations following out-patient surgeries.
Physical therapy—dates, duration referring physician and diagnosis.
Out-patient or in-patient drug rehabilitation treatment—dates, treating physicians, diagnoses and follow up visits. Medication associated or linked with these therapies.
Urgent Care/ER Visits—dates, duration, names of physicians, names of facilities, tests run, and diagnoses.
Admissions to hospitals or physician referrals resulting from urgent care/ER visits. Medications prescribed and procedures performed.
Ambulances/medical transportation—dates, number of times called in a span of time, diagnoses, treatment rendered by EMT.
Hospital Admissions
Name of hospital. Date of admission. Date of discharge. Admitting diagnosis and discharge diagnosis. List of complications. L.O.S.
Problems list. The names/times seen by specialists, their specialists and diagnoses by them. Time spent by each physician on every visit. The diagnoses or conditions for which they were seeing the patient.
Tests—lab tests, biopsies, surgical specimen exam, imaging tests and other tests with the dates and diagnoses and names of referring physicians and reporting physicians.
Treatment days in regular units. Treatment days in intensive care.
Post Hospitalization Management: ECF, NH, physical therapy, at home nurse visits, and infusion therapy.
Medication following discharge.
Ongoing complications, if any.
Readmission and readmission diagnoses and dates, dates of admission and discharge, treating physicians and their specialists and the time they spent with the patients in the hospital.

It should be appreciated that the above list is provided for purposes of example only, but that additional information may be obtained from the payor claims data 220.

It might at first appear implausible that transactional information, such as payor claims data 220, would provide meaningful medical or clinical information for inclusion in a PHR. However, payor claims data 220 creates a type of virtual medical record. Every claim which is processed typically includes, in addition to various demographic information, procedural or visit codes and diagnostic codes. Payor claims data 220 is generally more comprehensive relating to the encounters between the patients and different as well as diverse providers than the electronic medical records kept by individual providers since a health plan (or other payor) will generally receive claims from all or most of the significant care providers for an individual. Using the electronic medical records of the individual providers to assemble a PHR would, at best, be much more difficult, and would likely result in a record that is lacking in a full list of encounters, especially providers whose access was not provided for whatever reason. Another advantage to using the payor claims data 220 is that this data is relatively precise and orderly when compared to other data sources in the health care industry. The payor claims data 220 also provides a structure which is useful in methodically organizing and populating the data, and prioritizing the manner in which extracted data is displayed. In addition, the payor claims data 220 would not need coordination from the creators/keepers of the data. For example, the use of payor claims data 220 to add information about the hospital admission of a patient would not need the coordination of the hospital.

Preferably, the payor claims data 220 is "normalized" or placed into a standard format by a separate process. One such process is the Connect™ process available from the assignee of the present application. This process is described in U.S. patent application Ser. No. 10/381,158 entitled "System for Communication of Health Care Data" filed on Mar. 21, 2003 and claiming the benefit of PCT International Application No. PCT/US01/42618 filed on Oct. 11, 2001. Both U.S. and PCT applications are hereby expressly incorporated into this application by this reference thereto. Although specific to the payor from whom the payor claims data is obtained, the payor claims data 220 may be more readily utilized by the remainder of the PHR system 102 than "raw" data available from various health related organizations.

In the embodiment shown, the PHR population engine 202 has access to other health related data 222, which could be used to supplement and/or enhance the payor claims data 220. For example, the health related data 222 may be collected from patients using questionnaires. By way of another example, the health related data 222 may include clinical data obtained from various entities, such as hospitals, labs, imaging centers, or outpatient surgery centers. In addition, the health related information 40 could be obtained from physicians and/or physician offices.

In some embodiments, for example, individuals may be asked to complete questionnaires at the time of enrollment into a health plan, or at some later time when a PHR is being developed. The following is an illustrative example of information collected for a PHR using questionnaires:
General Information
Race.
Weight.
Change in Weight.
Height.
Blood Pressure.
History of diabetes, asthma, stroke, heart attack and other conditions.
History of Accident: automobile, motorcycle, bicycle and work-related.
History of potentially dangerous hobbies.
Family history of overweight, high blood pressure, diabetes, heart disease, cancer.
Lifestyle factors: smoking, alcohol, drugs, exercise and sports.
Visits to various countries where a disease could be contracted.
Any other history information that can be obtained by changing the questions and adding further questions.
Outpatient History
Vaccination history.
Mammography in women; retinal examinations for diabetics; colonoscopy for adults; PSA tests for males; etc.
Medications prescribed by specialists, with diagnoses. Duration of medication.

It should be appreciated that the above list is provided for purposes of example only, but that additional information may be obtained from patient questionnaires.

In some embodiments, the health related data 222 may include clinical data from hospitals, labs, imaging centers, outpatient surgery centers, and/or similar entities. In some cases, the clinical data may be extracted using a standard format. For example, this information is generally available in electronic form in Health Level Seven ("HL7") format and can be efficiently extracted through the use of interfaces designed for compatibility with this format. HL7 is a non-profit volunteer organization headquartered in Ann Arbor, Mich. that is an American National Standards Institute ("ANSI")-accredited Standards Developing Organization ("SDO") operating in the field of healthcare. This organization develops specifications that enable disparate healthcare applications to exchange key sets of clinical and administrative data. It should be appreciated that an interface may be provided to extract data from some other form or format. The following is an example list of clinical information that may be collected from the health related data 222:
Inpatient admission history and physical examination.
Inpatient discharge summary.
Selected lab results done during the hospital stay (some of the test results may be irrelevant for continuing care and may just add to the clutter).
Imaging test results.
Pathology reports, including reports of biopsies.
Medications administered to the patient.
Any other information which is considered relevant for continuing care.

It should be appreciated that the above list is provided for purposes of example only, but that additional clinical information may be obtained from various entities.

The manner in which such clinical information may be accessed will depend on the state of record keeping in each individual entity. In hospitals having relatively modern electronic medical record systems that use the HL7 format, for example, it should be relatively easy to gather the desired clinical information from the electronic medical record ("EMR") of each patient for each encounter. In hospitals without comprehensive EMR systems, or in those using different data formats, the information gathering may still take place, albeit through individually crafted interfaces or other means specific to the particular entities or data types. For example, lab, pathology reports and imaging tests results could be accessed by building interfaces specific to the systems used to maintain this data. The fact that many hospitals use outside vendors for such services, and an individual vendor may serve many hospitals, will allow an interface to be used across a number of providers. Similar solutions could be adopted with other types of clinical information. Relevant information may also be accessed through pharmacy systems, such as those maintained by hospitals or third parties. Admission history and physical examination and discharge summaries may also be accessed through transcription centers. This approach may be used with labs, imaging centers, outpatient surgery centers, and other entities. Many, if not most, of these entities have modern electronic systems, which are HL7 compatible, facilitating the gathering of relevant information. As discussed above, however, other techniques could be used to gather the information if not in HL7 format.

The health related data 222 may include information gathered from physicians and/or physician offices. There are thousands of physician-run clinical software systems in existence, with more variety and less standardization in record keeping than is the case with the other sources discussed above. One approach to obtaining information from physicians is to recognize what information is not available from payor claims data, questionnaire data and clinical data, and then focusing on obtaining that information. Typically, the information which this includes is relatively limited and consists mainly of results of some tests done in physician offices. Examples of such tests include EKG's, cardiac stress tests, echocardiogram tests, EEG's, EMG's, nerve conduction studies, and ultrasound tests done in physician offices. One possible approach to facilitate and incentivize physicians to provide this information to assist in building a patient's PHR is to ask or require providers to supply the information to a PHR portal. In some cases, for example, the supply of such information could be a condition for payment in connection with the subject tests.

In some embodiments, the PHR population engine 202 may interact with the correlation module 208 to correlate health related data 222 and/or payor claims data 220 with a health care concept in an arrangement of health care concepts. Preferably, the correlation module 208 encodes the health related data 222 and/or payor claims data 220 into SNOMED ("Systematic Nomenclature of Medicine") codes. The SNOMED codes or health related data based on the SNOMED codes may be inserted into the patient's PHR. In some embodiments, other health entries in the PHR relating to the SNOMED code could be associated in the PHR, regardless of the format or mechanism from which the information is derived. By using SNOMED codes in the PHR, differing types of entries, such as illness/conditions, procedures, care plans, biometric trackers, medication profile and lab results, could be tied together for better decision making, data analysis, application of permissions and enhanced health tracking.

SNOMED is a division of the College of American Pathologists ("CAP"). SNOMED Clinical Terms ("SNOMED CT") is a scientifically-validated, clinical health care terminology and infrastructure. Health data can be captured, shared and aggregated in a consistent manner by the SNOMED CT terminology. The terminology currently contains over 350,000 hierarchically specified health care concepts, each with unique meanings and logic-based definitions. Additionally, these health care concepts have distinct relationships that support reliability and consistency for data retrieval. In some embodiments, the correlation module 208 may be associated with a correlation table 210, which may map health related data 222 and/or payor claims data 220 into a health care concept, such as a SNOMED code.

FIG. 9 provides an example with a PHR for a patient identified as "Ann Smith." In this example, the PHR includes a MPI field, which contains the MPI associated with Ann Smith, as discussed above. The example PHR includes diagnosis, procedure, and medication fields in which the SNOMED codes derived from ICD codes, CPT codes and NDC codes, respectively, may be stored. In the example shown, the payor claims data 220 is the ICD9 code of 250.00. The correlation module 208 could correlate this ICD9 code into the diabetes concept. The PHR population engine 202 may include the SNOMED code associated with the diabetes concept into the diagnosis field of the PHR for Ann Smith. Other health entries in the PHR relating to diabetes could be associated with this entry in the PHR, regardless of the format or mechanism from which the information is derived, whether from an ICD code, a CPT code, a NDC number or manually entered data. Physicians, patients and others could then categorize information related to specific health concepts using the SNOMED codes, including visits, illness/ conditions, procedures, immunizations, medications, health action plans, lab results or other related data. The use of the MPI field could further enhance the PHR system 102. Since the MPI identifies the patient and the SNOMED code designates the health concept, the PHR system 102 may collect and present diverse data in a PHR that can be organized, stored, viewed, and managed by all interested parties in health care transactions.

The PHR system 102 may include an access management module 216. The access management module may provide an interface to the PHR system 102 for client systems 106, to enhance and/or supplement the access provided by the messaging facility 214. In some embodiments, for example, the access management module 216 may provide a web-based portal to access PHRs in the PHR database 200.

In some embodiments, for example, a patient may access his/her PHR via the web-based portal (or through another connection to the PHR system 102). This would allow the patient to supplement his/her PHR with additional information, such as over the counter medications, allergies, immunizations, etc. The patient could also view his/her PHR using the access management module 216. For example, the patient could view a diagnosis, laboratory results and other information in his/her PHR via the web-based portion (or other connection). In some circumstances, the timing of patient access to certain records in the PHR may be controlled. For example, a physician may not want a patient to view the lab results until the physician has reviewed the lab results. Accordingly, in some embodiments, the access management module 216 may be configured to determine whether records in the PHR have been "released" for patient access. If not, the access management module 216 would not allow the patient to view any "unreleased" entries, but only allow access to "released" records.

In some embodiments, the access management module 216 may interact with a security module 204 that restricts access to PHRs in the PHR database 200. For example, some providers may not be granted access to portions of the patient's PHR that may be considered sensitive. Whenever a user accesses a patient's PHR, the security module 204 may evaluate whether permission has been granted to that user so that only the information contained in the PHR to which that user has been granted permission will be displayed. The use of the security module 204 in this manner allows a patient to completely control access to his/her PHR. For example, the patient may specify the default permissions for various types of entities, including his/her spouse, family members, primary care physicians, and other health care providers. The term "health care provider" is intended to be broadly construed to include any persons who provide health care as part of their job responsibilities. In some embodiments, the patient may specify the particular individuals to whom permissions may be granted. The use of permissions addresses privacy concerns of patients, which may allow a higher level of usage, as well as better care resulting from more patients sharing data electronically with their healthcare providers via the PHR.

In some embodiments, portions of the PHRs may be protected by the security module 204 based on the types of health information that a patient may consider sensitive. For example, a patient may elect to allow the designed physician to have full access to their various illness/condition list, while restricting access to selected diseases, such as sexually transmitted diseases or psychological disorders. If a portion of the PHR relates to an area that may be considered sensitive, the security module 204 may consider that area of the PHR to be a protected data class. For example, information in a PHR related to reproductive health, mental health, HIV, genetic testing, abortion, sexually transmitted diseases, alcohol abuse, drug abuse, AIDS, contraceptive issues, abuse or neglect, sexual assault and/or other sensitive health issues may be considered protected data classes. Embodiments are contemplated in which a predefined list of sensitive health issues could be considered protected data classes. Of course, it should be appreciated that additional data classes could be added and/or deleted from the list of protected data classes. In some embodiments, the correlation of payor claims data and/ or health related data into SNOMED codes, as described herein, may be used to categorize the PHR into protected classes for restricting access to the PHR. For example, each SNOMED code related to HIV could be associated with the HIV protected class.

Embodiments are also contemplated in which the security module 204 may restrict access based on functional areas of a PHR. By way of example, function areas of a PHR may include summary, health risk assessment, health calendar, medical history, medication profile, visit summary, health event record, illness and conditions, my plan for health, account summary, benefits and eligibility, change PCP, claims, member information, referrals and authorizations, permissions.

The security module 204 may allow a patient to select entities that may access protected data classes and/or functional areas of his/her PHR. Embodiments are contemplated in which a patient may revoke consent, which would prevent electronic retrieval of his/her PHR. In some embodiments, a patient may restrict access to certain protected data classes and/or functional areas. It should be appreciated that there could be a variety of reasons for a patient to restrict access to protected data classes and/or functional areas. For example, a patient may not want clinician specialists to see information not related to their specialty, or may not want a spouse (or other family member) to view medication information. In some embodiments, the security module 204 may provide an error message if access to a restricted area is attempted. In some cases, the protected data classes and/or functional areas that have been restricted may not be displayed, which would prevent an entity being restricted from realizing that a restriction is in place. If a spouse of a patient reviewed his/her PHR, for example, the protected data classes from which the spouse was restricted may not be visible to the spouse; accordingly, the spouse would not know that a restriction to accessing the PHR was in place.

FIG. 10 shows an example interface that allows a patient to restrict access to portions of his/her PHR. In this example, the patient has selected the access rights for a healthcare provider called "Doctor Allbetter." As shown, the patient has revoked Doctor Allbetter's access to all protected data classes, except information related to mental health. In addition, the patient has revoked Dr. Allbetter's access to all functional areas, In some embodiments, default access rights to a PHR may be established. For example, a payor may define default access rights for each of its members. Embodiments are contemplated in which the default access rights could be based on various factors, such as relationship, gender, age and location of the patient. In this manner, a reasonable level of access rights based on the patient could be established, even before the patient customizes the access rights as discussed above.

Embodiments are contemplated in which the security module 204 may include role-based security. In such embodiments, the users may be assigned a role to define the portions of the PHRs to which the user has access. This eliminates the need to establish security access levels separately for each user. For example, each role may include a security profile defined by the organization that the data that would be accessed. By way of another example, heath plan data may be protected by the role that the health plan defines for the user, while the hospital data may be protected by a role that the hospital has defined.

In some embodiments, the security module 204 may permit a restriction to be overridden in certain circumstances. For example, this may allow a physician to view a restricted portion of a PHR for emergency care. By allowing some restrictions to be overridden in certain circumstances, this balances privacy concerns with the possible need for emergency care where PHR data is required due to the state of the patient.

As shown in FIG. 11, for example, a user may be presented with a window showing that permission has not been granted to the portion of the PHR for which access is sought, but that the restriction may be overridden. In this example, the word "here" in the window is a hyperlink that allows the user to override the restriction. It should be appreciated that FIG. 11 is provided for purposes of example, but that numerous different types of user interfaces could be used to allow a restriction to be overridden.

In some embodiments, the user may be required to provide a reason for overriding a restriction. For example, as shown in the illustrative embodiment in FIG. 12, the user may be allowed to select from a list of possible reasons for overriding the restriction and/or manually enter a reason. This reason, along with other information regarding the override, may be stored by the security module 204, as described herein with respect to auditing of the PHR.

The security module 204 may create an audit trail regarding access to a patient's PHR. For example, the audit may include when permission was granted, who was granted permission, who recorded the granting of the permission and what permissions were granted. In some embodiments, the security module 204 may audit whenever a user accesses a patient's PHR. For example, the audit may include when a patient's PHR is accessed, who accessed a patient's PHR and what portions of the PHR were accessed. In some embodiments, the audit and permission data may be stored in the security database 206 and/or in the PHR database and/or other storage location.

FIG. 13 shows an example audit report based on information gathered by the security module 204. In this example report, the user "Doctor Allbetter" has accessed the PHR of a patient called "Ann Smith" on four occasions. Each time that Doctor Allbetter accessed Ann Smith's PHR, the audit report notes the date and time that the PHR was accessed. For information in the PHR to which Doctor Allbetter had access, the example report includes a "permission type" column and a column with the reason for accessing the PHR. In this example, the first time Doctor Allbetter accessed the PHR, he/she had consent to access that portion of the PHR. In each of the other three occasions, Doctor Allbetter overrode the permissions to access a functional area (shown as "FA") and a protected data class (shown as "PDC") as part of emergency care.

In some embodiments, the PHR system 102 may include a data analysis module 212. The data analysis module 212 could be configured to identify patterns or relationships in data contained in the PHR database 200 for a single patient or across multiple patients. For example, the data analysis module 212 could perform population studies across many healthcare events, such as condition, progress of condition, impact of co-morbidities on the underlying condition, procedures and medications. Due to the plurality of PHRs in the PHR database 200, the data analysis module could analyze data relating to a large number of patients. The data analysis module 212 could provide an outcomes measurement. For example, the data analysis module 212 could identify the medications that were the most successful in controlling diabetes. By way of another example, the data analysis module 212 could compare the results of surgery versus medical treatment. By way of another example, the data analysis module 212 could analyze surveys in the PHR database 200 regarding the effectiveness of treatments, drugs, etc.

In embodiments in which SNOMED encoding is used, as described herein, the data analysis module 212 could use SNOMED codes as a mechanism to tie events together, to identify patterns or relationships. For example, the use of SNOMED codes in the PHR database 200 aids in outcomes measurements because healthcare events, such as conditions, procedures, medications, and survey information, could be tied to related SNOMED codes. By way of example, survey results covering the effectiveness of chiropractic care for back pain could be measured, as well as the effectiveness of wellness programs. The use of an MPI could also aid in data analysis. For example, the use of an MPI ensures that all episodes of care, as well as each clinical event from the various data sources, are collected and appropriately stored with the correct patient. By collecting all relevant healthcare information for a patient, data analysis is greatly enhanced as compared to traditional approaches. Most pertinent is the ability to compare data from different events that may have come from different sources. For example, the data analysis module 212 could determine how many patients that on taking a particular medication are subsequently treated for a particular condition, for example. By way of another example, the data analysis module 212 could analyze how many patients that have had a given surgical procedure had been given a follow-up laboratory procedure.

In some embodiments, the PHR system 102 may include a filtering module 218. The filtering module 218 may be configured to change modes to vary the resolution of data that is viewed by a user. By "resolution" it is meant that the filtering module 218 may filter the patient data to provide either a higher level view or a lower level view of data in a PHR. For example, consider data in a PHR related to an optic condition. If the filtering module 218 were configured to provide a higher level view, the optic condition may be described merely as "an optic condition." If the filtering module 218 were configured to provide a lower level view, the optic condition may be described as a "staphylococcal eye infection."

In some embodiments, the filtering module 218 may be configured to traverse up and down the SNOMED hierarchy to adjust the resolution of data that is viewed by the user. For example, if the filtering module 218 were configured for the lowest level view, the user may view a description associated with the SNOMED code. If the filtering module 218 were configured for a higher level view, the user may view a description associated with a more generalized code related to the SNOMED code stored in the patient's PHR. For example, if the filtering module 218 were configured for a high level view, and the SNOMED concept related to the SNOMED code in the PHR were "kidney disease," the user may view the more generalized SNOMED concept described as "disorder of the urinary system."

In some embodiments, the filtering module 218 may be configured to filter patient data based on the type of user accessing the information. For example, the filtering module 218 may filter patient data unrelated to the specialty of the physician accessing the PHR database 200. In such an embodiment, physicians may be associated with a specialty code, such as an X12 code, based on the specialty of the physician. A cross-reference table (or other lookup function) may be provided to determine the relevant SNOMED codes based on the specialty code of the physician accessing the patient data. In this manner, the physician will not be overloaded with voluminous patient data, but will be presented with patient data relevant to his/her specialty. Of course, the physician may instruct the filtering module 218 to reveal additional patient data that may not be associated with his/her specialty.

Embodiments are contemplated in which various synonyms may be associated with each medical concept in the PHR. For example, each PHR in the PHR database 200 may include synonyms or synonymous descriptions for one or more entries in the PHR that describe the same medical concept, such as a condition, procedure, etc., using varying terminology. The filtering module 218 may display the synonym that is best suited to the type of user accessing the PHR. Embodiments are contemplated in which certain descriptions may use medical terminology while another description may use layman's terms. For example, a patient accessing his/her PHR may view an entry as "Heart Attack" while a healthcare provider accessing the same entry may view "myocardial infarction." This allows patients to view the PHR using consumer friendly terms whereas health care providers, such as physicians and nurses, can view detailed medical terms.

Figure 14:
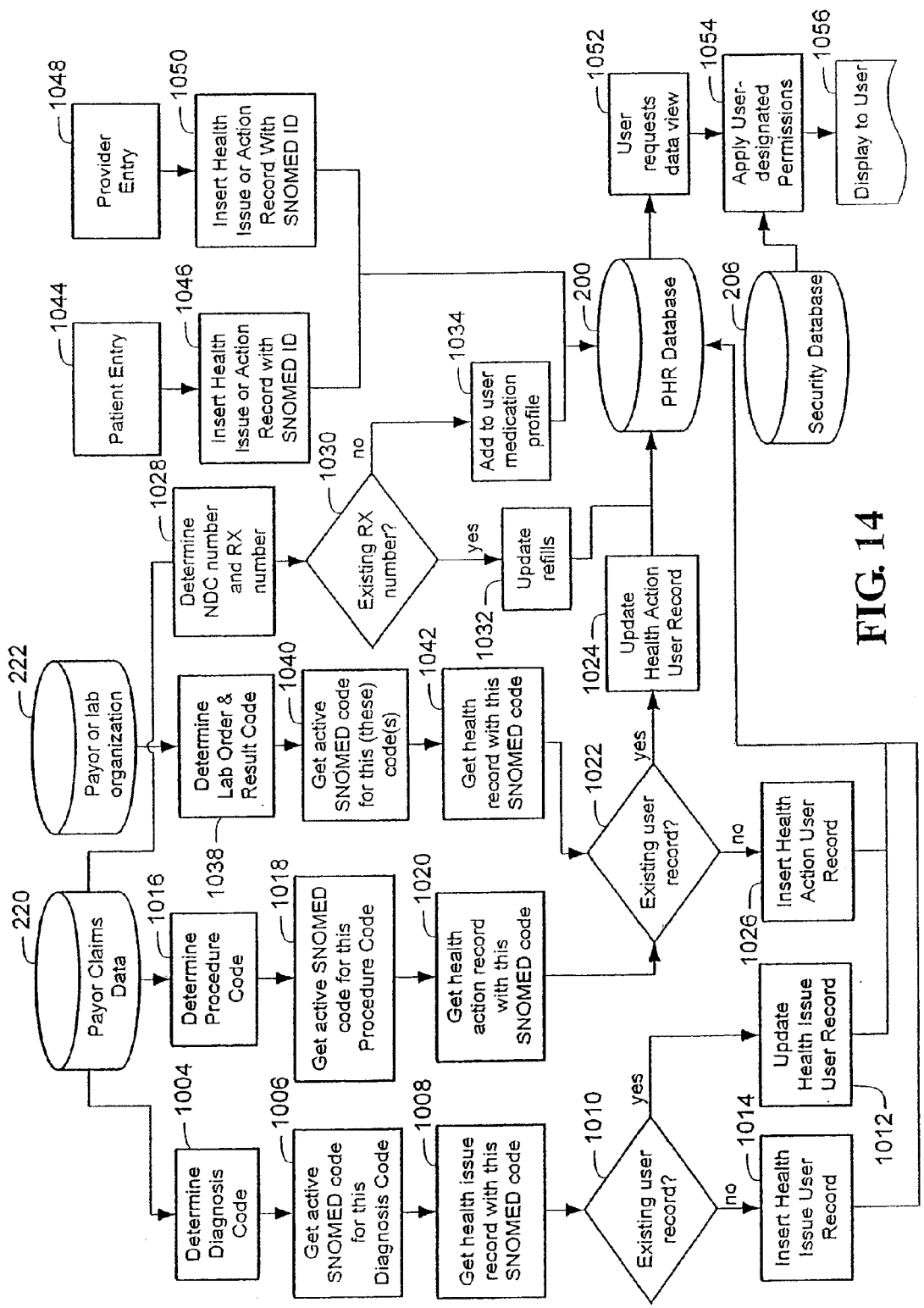
FIG. 14 shows a flow chart which illustrates an embodiment of a system and method for populating a personal/individual health record with data.

FIG. 14 is a diagram showing acts that may be performed by the PHR System 102. In some embodiments, the PHR system 102 may access or be provided with payor claims data 220. In some embodiments, the payor claims data 220 could be comprehensively coded using the SNOMED codes. Using the payor claims data 220, the PHR system 102 may determine, for a selected individual and PHR, the diagnosis code associated with a particular claim. For example, the ICD 9 ("International Classification of Diseases, 91h Revision") code may be determined. This operation is represented by process block 1004. Following this step, the PHR system 102 may retrieve the SNOMED code associated with the diagnosis code. This operation is represented by process block 1006.

Next, as illustrated by process block 1008, a health issue record associated with the SNOMED code may be retrieved. The PHR system 102 may then determine, in decision operation 1010, whether the subject information is already described in an existing user record. If so, the PHR system 102 updates the data, as shown in operation 1012. If not, the PHR system 102 adds this information to the user's PHR, as illustrated by process block 1014. If not, the PHR system 102 populates the user's record with the identified health issue.

In addition to handling diagnosis codes, such as ICD 9 codes, the PHR system may also determine procedure codes, such as CPT ("Current Procedural Terminology") codes, from each unique claim present in the payor claims data 220. (Process Block 1016). As illustrated by process block 1018, the PHR system 102 may retrieve the SNOMED code associated with the subject procedure coded (e.g., CPT code). Following this step, a health action record associated with the subject SNOMED code may be retrieved, as illustrated by process block 1020. The PHR system 102 may then determine, in decision operation 1022, whether the user has this health action as an existing entry. If so, the PHR system 102 updates the data in process block 1024. If not, the PHR system 102 adds this information to the user's PHR, as illustrated by process block 1026.

In some embodiments, the PHR system 102 may be configured to populate a PHR with prescription related information in the payor claims data 220. Process block 1028 represents the operation of determining the NDC ("National Drug Code") number and prescription number for medications identified in the payor claims data. After this information is identified, the PHR system 102 determines, in decision operation 1030, whether the user has this medication or prescription as an existing entry associated with this provider. If yes, refill information is updated, as indicated by process block 1032, as necessary. If no, the PHR system 102 recognizes this information as being new information and adds it to the medication profile in the PHR of the subject user, as indicated by processor block 1034.

In some embodiments, the PHR system 102 may be configured to populate and/or update a PHR using health-related data 222 from an entity (e.g., payor or laboratory organization) other than payor claims data 220. Process block 1038 represents the operation of determining the lab order and/or result code from the health related data 222. As illustrated by process block 1040, the PHR system 102 may retrieve the SNOMED code(s) associated with the code(s). Following this step, a health action record associated with the subject SNOMED code(s) may be retrieved, as illustrated by process block 1042. The PHR system 102 may then determine, in decision operation 1022, whether the user has this health action as an existing entry. If so, the PHR system 102 updates the data in process block 1024. If not, the PHR system 102 adds this information to the user's PHR, as illustrated by process block 1026. In some embodiments, the data from which the SNOMED code is derived (e.g., ICD 9 code, CPT code, NDC code, lab order and/or result code, directly entered data) may be captured for auditing purposes, as this would provide an explanation of the information from which the SNOMED was derived. It should be appreciated that information, other than a SNOMED code, could be derived from the data received from the PHR system 102. For example, the location, type of service, service dates, servicing provider, requesting provided, could also be derived from the payor claims data and/or health related data received from the PHR system 102.

Process block 1044 represents an operation whereby the user can enter information into his or her PHR. This information is preferably entered via an interface that guides the user through the addition of health record entries in such a manner as to capture and classify the appropriate SNOMED code, such as the Connect™ application marketed by the assignee of the present application. Following the entry of this information by the user, the PHR system 102 inserts a corresponding health issue or action into the user's PHR, as illustrated by process block 1046.

Similarly, a health care provider (or other entity) may enter information into the PHR of a selected user, as indicated by process block 1048. This information is also preferably entered via an interface like the Connect™ software. Following entry, a health issue or action is inserted into the provider's PHR, as illustrated by process operation 1050.

Following entry of all health issues or actions by the PHR system 102, as discussed above, the subject issues and actions are stored and tracked in the PHR database 200. One such data base is provided as part of the Connect™ application referenced above. An application-specific identifier may be assigned to each member by the Connect™ software.

Process block 1052 illustrates the processing of an access request by a member or user (i.e., one of the individuals for whom a PHR is stored and maintained by the PHR system). A properly logged on and identified user can access the information stored in a PHR stored in PHR database 200. As discussed herein, the PHR system 102 may verify permission of the user as to the requested portion of the PHR, as indicated by process block 1054 and the security database 206. The subject information can be displayed in a variety of formats and using a variety of display to technologies, as illustrated by block 1056.

It is appreciated that embodiments may include a computer system that extracts healthcare data from one or more payers to identify meaningful relationships or patterns and treatments from a payer or multiple payers to compare the effectiveness of treatments of particular diseases and determine the effectiveness of various treatments of those diseases to allow setting up and modifying clinical protocols for optimal care. These improved protocols can be made available at the point of care to improve care, case and disease management. Integrating administrative data with clinical information such as lab results and prescriptions in normalized form can be used to improve medical management, disease management and HEDIS measurements.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

As should be appreciated by one of skill in the art, the present invention may be embodied in many different forms, such as one or more devices, methods, data processing systems or program products. Accordingly, embodiments of the invention may take the form of an entirely software embodiment or an embodiment combining hardware and software aspects. Furthermore, embodiments of the invention may take the form of a computer program product on a computer-readable storage medium having computer-readable program code embodied in the storage medium. Any suitable storage medium may be utilized including read-only memory ("ROM"), RAM, DRAM, SDRAM, hard disks, CD-ROMs, DVD-ROMs, any optical storage device, and any magnetic storage device.

Although the systems have been described with reference to particular means, materials and embodiments, from the foregoing description, one skilled in the art can easily ascertain the essential characteristics of the illustrative system and various changes and modifications may be made to adapt the various uses and characteristics without departing from the spirit and scope of the present invention as described by the claims which follow.

What is claimed is:

1. A computer system that extracts health care data from one or more health care payors to identify meaningful relationships or patterns in treatments to compare the effectiveness of various treatment of specific diseases, the computer system comprising:
   a computer configured to communicate with one or more payor computer systems from one or more payors over the Internet;
   wherein the payor computer systems are of a type that includes one or more databases storing records of the health care data;
   wherein a normalized format is of a type that displays health care data from one or more sources such that any health care data having the same meaning will be expressed in the same format despite any prior formatting;
   a staging database in communication with the computer;
   wherein the staging database is configured to receive the health care data from each of the payor computer systems;
   wherein the health care data from each of the payor computer systems is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format; and
   wherein the normalized data is made available to determine comparative effectiveness of various treatments of specific diseases.

2. A computer system that extracts health care data from one or more health care payors to identify meaningful relationships or patterns in treatments across multiple payors to compare the effectiveness of various treatments of specific diseases, the computer system comprising:
   a computer configured to communicate with one or more payor computer systems from one or more payors over the Internet;
   wherein the payor computer systems are of a type that includes one or more databases storing records of the health care data;
   wherein a normalized format is of a type that displays health care data from one or more sources such that any health care data having the same meaning will be expressed in the same format despite any prior formatting;
   a staging database in communication with the computer;
   wherein the staging database is configured to receive the health care data from each of the payor computer systems;
   wherein the health care data from each of the payor computer systems is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format; and wherein the normalized data is made available to determine comparative effectiveness of various treatments of specific diseases and to allow to set up or modify clinical protocols for optimal care.

3. A computer system that extracts health care data from a health care payor to identify meaningful relationships or patterns in treatments which are not optimal for quality care, the computer system comprising:

a staging database in communication with the computer configured to receive health care data from a payor legacy computer system;

wherein the payor legacy computer system is of a type that includes one or more databases storing records of the health care data;

wherein a normalized format is of a type that displays health care data from one or more sources such that any health care data having the same meaning will be expressed in the same format despite any prior formatting;

wherein the health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format; and wherein the normalized data is made available to set up or modify clinical care management protocols to deliver optimal care.

4. A computer system that extracts health care data from a health care payor to identify meaningful relationships or patterns in treatments across multiple providers for improving quality of care, the computer system comprising:

a staging database configured to receive health care data from a payor legacy computer system;

wherein the payor legacy computer system is of a type that includes one or more databases storing records of the health care data;

wherein a normalized format is of a type that displays health care data from one or more sources such that any health care data having the same meaning will be expressed in the same format despite any prior formatting;

wherein the health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format; and wherein the normalized data is made available to allow to set up or modify a case management based on clinical protocols to provide optimal care.

5. A computer system that extracts health care data from a health care payor to identify meaningful relationships or patterns in treatments of chronic diseases which may be suboptimal, the computer system comprising:

a staging database configured to receive health care data from a payor legacy computer system;

wherein the payor legacy computer system is of a type that includes one or more databases storing records of the health care data;

wherein a normalized format is of a type that displays health care data from one or more sources such that any health care data having the same meaning will be expressed in the same format despite any prior formatting;

wherein the health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format; and wherein the normalized data is made available to improve disease management of chronic diseases.

6. A computer system that identifies meaningful relationships or patterns in treatments to identify effectiveness of specific treatments of diseases for improving quality of care, the computer system comprising:

a computer that includes one or more records of health care data and configured to convert the health care data into a normalized format;

wherein a normalized format is of a type that displays health care data from one or more sources such that any health care data having the same meaning will be expressed in the same format despite any prior formatting;

wherein converting the health care data into the normalized format is done so by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format; and wherein the normalized data is made available to determine effectiveness of various specific disease treatments to identify effective disease treatments for cost and quality of care.

7. A computer system that identifies meaningful relationships or patterns in treatments to identify effectiveness of specific treatments of diseases for improving quality of care, the computer system comprising:

a computer configured to communicate with a payor computer system over the Internet;

wherein the payor computer system is of a type that includes one or more databases storing records of the health care data;

wherein a normalized format is of a type that displays health care data from one or more sources such that any health care data having the same meaning will be expressed in the same format despite any prior formatting;

a staging database in communication with the computer;

wherein the staging database is configured to receive the health care data from the payor computer system;

wherein the health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format;

wherein the normalized data includes health care payor data; and wherein the normalized data is made available to determine effectiveness of various specific disease treatments to identify effective disease treatments for cost and quality of care to allow clinical protocols to be set up to optimize care.

8. A computer system that identifies meaningful relationships or patterns in treatments to identify effectiveness of specific treatments of diseases for improving quality of care, the computer system comprising:

a computer configured to communicate with payor computer system over the Internet;

wherein the payor computer system is of a type that includes one or more databases storing records of the health care data;

wherein a normalized format is of a type that displays health care data from one or more sources such that any health care data having the same meaning will be expressed in the same format despite any prior formatting;

a staging database in communication with the computer;

wherein the staging database is configured to receive the health care data from the payor computer system;

wherein the health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format;

wherein the normalized data includes health care provider data; and wherein the normalized data is made available to determine effectiveness of various specific disease treatments to identify effective disease treatments for cost and quality of care to allow clinical protocols to be set up to optimize care.

9. A computer system that identifies meaningful relationships or patterns in treatments to identify effectiveness of specific treatments of diseases for improving quality of care, the computer system comprising:

a computer configured to communicate with a payor computer system over the Internet;

wherein the payor computer system is of a type that includes one or more databases storing records of the health care data;

wherein a normalized format is of a type that displays health care data from one or more sources such that any health care data having the same meaning will be expressed in the same format despite any prior formatting;

a staging database in communication with the computer;

wherein the staging database is configured to receive the health care data of the payor computer system;

wherein the health care data from the payor computer system is configured to be converted into the normalized format by a normalization system comprising: a rules engine that predetermines how each of the health care data is to appear in its respective field, and remodels any health care data not expressed as predetermined by the normalized format into the normalized format becoming normalized data such that all normalized data expressing information having the same meaning now expresses that meaning in the same format;

wherein the normalized data includes health care claims data; and wherein the normalized data is made available to determine effectiveness of various specific disease treatments to identify effective disease treatments for cost and quality of care to allow clinical protocols to be set up to optimize care.

* * * * *